United States Patent
Huang

(10) Patent No.: US 8,999,935 B2
(45) Date of Patent: Apr. 7, 2015

(54) TREATMENT OF OSTEOPOROSIS IN PERI- AND POST-MENOPAUSAL WOMEN WITH HEPCIDIN

(75) Inventor: Xi Huang, Fair Lawn, NJ (US)

(73) Assignee: New York University, New York, NY (US)

( * ) Notice: Subject to any disclaimer, the term of this patent is extended or adjusted under 35 U.S.C. 154(b) by 311 days.

(21) Appl. No.: 12/704,187

(22) Filed: Feb. 11, 2010

(65) Prior Publication Data

US 2010/0204122 A1 Aug. 12, 2010

Related U.S. Application Data

(60) Provisional application No. 61/151,648, filed on Feb. 11, 2009.

(51) Int. Cl.
| | |
|---|---|
| *A61K 38/16* | (2006.01) |
| *A61K 38/17* | (2006.01) |
| *A61K 38/22* | (2006.01) |
| *A61P 19/08* | (2006.01) |
| *A61P 19/10* | (2006.01) |
| *C07K 14/575* | (2006.01) |
| *A61K 31/711* | (2006.01) |

(52) U.S. Cl.
CPC ............ *A61K 31/711* (2013.01); *A61K 38/22* (2013.01)

(58) Field of Classification Search
None
See application file for complete search history.

(56) References Cited

U.S. PATENT DOCUMENTS

| 7,169,758 B2 | 1/2007 | Nicolas et al. |
| 2007/0275913 A1 | 11/2007 | Monia et al. |
| 2008/0213277 A1 | 9/2008 | Sasu et al. |

FOREIGN PATENT DOCUMENTS

| WO | WO 00/23594 | * | 4/2000 |

OTHER PUBLICATIONS

Nemeth et al., Blood, 2006, vol. 107(1):328-333.*
Kamai et al., BMC Cancer, 2009, vol. 9:270.*
Babitt et al., Nature Genetics, 2006, vol. 38(5):531-539.*
Liu et al., Biometals, 2006, vol. 19(3):245-251.*
Valore et al., Blood Cells, Molecules, and Diseases, 2008, vol. 40(1):132-138.*
Atanasiu et al., "Hepcidin—Central Regulator of Iron Metabolism," European Journal of Haematology 78:1-10 (2006).
Collins et al., "Hepcidin Regulation of Iron Transport," J. Nutr. 138:2284-2288 (2008).
Ganz et al., "Immunoassay for Human Serum Hepcidin," Blood 112(10):4292-4297 (2008).
Naot et al., "Lactoferrin—A Novel Bone Growth Factor," Clinical Medicine & Research 3(2):93-101 (2005).
Nemeth et al., "The N-terminus of Hepcidin is Essential for its Interaction with Ferroportin: Structure-function Study," Blood 107(1):328-333 (2006).
Nemeth et al., "Regulation of Iron Metabolism by Hepcidin," Annu. Rev. Nutr. 26:323-42 (2006).

* cited by examiner

*Primary Examiner* — Xiaozhen Xie
(74) *Attorney, Agent, or Firm* — LeClairRyan, a Professional Corporation

(57) ABSTRACT

The present invention is directed to a method of treating, preventing, or reducing the risk of bone deterioration or osteoporosis in a peri- or post-menopausal female subject. The method involves selecting a peri- or post-menopausal female subject in need of treating, preventing, or reducing the risk of bone deterioration or osteoporosis and administering hepcidin to the selected subject under conditions effective to treat, prevent, or reduce the risk of bone deterioration or osteoporosis.

7 Claims, 29 Drawing Sheets

```
                              SEQUENCE LISTING

<160> NUMBER OF SEQ ID NOS: 34

<210> SEQ ID NO 1
<211> LENGTH: 25
<212> TYPE: PRT
<213> ORGANISM: Artificial
<220> FEATURE:
<223> OTHER INFORMATION: Synthetic designed polypeptide
<220> FEATURE:
<221> NAME/KEY: MISC_FEATURE
<222> LOCATION: (1)..(1)
<223> OTHER INFORMATION: Xaa at position 1 is Asp, Gln, or absent
<220> FEATURE:
<221> NAME/KEY: MISC_FEATURE
<222> LOCATION: (2)..(2)
<223> OTHER INFORMATION: Xaa at position 2 is Thr, Ile, Ser, or absent
<220> FEATURE:
<221> NAME/KEY: MISC_FEATURE
<222> LOCATION: (3)..(3)
<223> OTHER INFORMATION: Xaa at position 3 is Asn, His, or absent
<220> FEATURE:
<221> NAME/KEY: MISC_FEATURE
<222> LOCATION: (4)..(4)
<223> OTHER INFORMATION: Xaa at position 4 is Phe, Leu, or absent
<220> FEATURE:
<221> NAME/KEY: MISC_FEATURE
<222> LOCATION: (5)..(5)
<223> OTHER INFORMATION: Xaa at position 5 is Pro, Ser, or absent
<220> FEATURE:
<221> NAME/KEY: MISC_FEATURE
<222> LOCATION: (6)..(6)
<223> OTHER INFORMATION: Xaa at position 6 is Leu or Ile
<220> FEATURE:
<221> NAME/KEY: MISC_FEATURE
<222> LOCATION: (7)..(7)
<223> OTHER INFORMATION: Xaa at position 7 is Cys, Ala, or Tyr
<220> FEATURE:
<221> NAME/KEY: MISC_FEATURE
<222> LOCATION: (8)..(8)
<223> OTHER INFORMATION: Xaa at position 8 is Ile, Leu, Thr, or Arg
<220> FEATURE:
<221> NAME/KEY: MISC_FEATURE
<222> LOCATION: (9)..(9)
<223> OTHER INFORMATION: Xaa at position 9 is Phe or Leu
<220> FEATURE:
<221> NAME/KEY: MISC_FEATURE
<222> LOCATION: (12)..(12)
<223> OTHER INFORMATION: Xaa at position 12 is Lys, Gly, Asp, or Gln
<220> FEATURE:
<221> NAME/KEY: MISC_FEATURE
<222> LOCATION: (15)..(15)
<223> OTHER INFORMATION: Xaa at position 15 is Asn, His, Arg, or Lys
<220> FEATURE:
<221> NAME/KEY: MISC_FEATURE
<222> LOCATION: (16)..(16)
<223> OTHER INFORMATION: Xaa at position 16 is Asn, Thr, Gln, Lys, or
      Arg
<220> FEATURE:
<221> NAME/KEY: MISC_FEATURE
<222> LOCATION: (17)..(17)
<223> OTHER INFORMATION: Xaa at position 17 is Pro, Gln, Ser, Ala, Lys,
      or Gly
<220> FEATURE:
<221> NAME/KEY: MISC_FEATURE
```

```
<222> LOCATION: (18)..(18)
<223> OTHER INFORMATION: Xaa at position 18 is Gln, Gly, Ser, Lys, Asn,
      Thr, or Ile
<220> FEATURE:
<221> NAME/KEY: MISC_FEATURE
<222> LOCATION: (21)..(21)
<223> OTHER INFORMATION: Xaa at position 21 is Ile, Leu, Phe, Tyr, Met,
      or Trp
<220> FEATURE:
<221> NAME/KEY: MISC_FEATURE
<222> LOCATION: (23)..(23)
<223> OTHER INFORMATION: Xaa at position 23 is Cys or Ala
<220> FEATURE:
<221> NAME/KEY: MISC_FEATURE
<222> LOCATION: (24)..(24)
<223> OTHER INFORMATION: Xaa at position 24 is Lys, Ile, Arg, Glu, or
      absent
<220> FEATURE:
<221> NAME/KEY: MISC_FEATURE
<222> LOCATION: (25)..(25)
<223> OTHER INFORMATION: Xaa at position 25 is Thr, Phe, Glu, or absent

<400> SEQUENCE: 1

Xaa Xaa Xaa Xaa Xaa Xaa Xaa Xaa Xaa Cys Cys Xaa Cys Cys Xaa Xaa
1               5                   10                  15

Xaa Xaa Cys Gly Xaa Cys Xaa Xaa Xaa
            20                  25

<210> SEQ ID NO 2
<211> LENGTH: 25
<212> TYPE: PRT
<213> ORGANISM: Homo sapiens

<400> SEQUENCE: 2

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 3
<211> LENGTH: 25
<212> TYPE: PRT
<213> ORGANISM: Homo sapiens

<400> SEQUENCE: 3

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 4
<211> LENGTH: 25
<212> TYPE: PRT
<213> ORGANISM: Homo sapiens

<400> SEQUENCE: 4

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 5
<211> LENGTH: 25
<212> TYPE: PRT
<213> ORGANISM: Pan troglodytes

<400> SEQUENCE: 5
```

-continued

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 6
<211> LENGTH: 25
<212> TYPE: PRT
<213> ORGANISM: Presbytis melalophos

<400> SEQUENCE: 6

Asp Thr His Phe Pro Ile Cys Ile Phe Cys Cys Gly Cys Cys His Arg
1               5                   10                  15

Ser Lys Cys Gly Met Cys Cys Arg Thr
            20                  25

<210> SEQ ID NO 7
<211> LENGTH: 25
<212> TYPE: PRT
<213> ORGANISM: Trachypithecus cristatus

<400> SEQUENCE: 7

Asp Thr His Phe Pro Ile Cys Ile Phe Cys Cys Gly Cys Cys His Arg
1               5                   10                  15

Ser Lys Cys Gly Met Cys Cys Arg Thr
            20                  25

<210> SEQ ID NO 8
<211> LENGTH: 25
<212> TYPE: PRT
<213> ORGANISM: Trachypithecus obscurus

<400> SEQUENCE: 8

Asp Thr His Phe Pro Ile Cys Ile Phe Cys Cys Gly Cys Cys His Arg
1               5                   10                  15

Ser Lys Cys Gly Met Cys Cys Arg Thr
            20                  25

<210> SEQ ID NO 9
<211> LENGTH: 25
<212> TYPE: PRT
<213> ORGANISM: Gorilla gorilla

<400> SEQUENCE: 9

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 10
<211> LENGTH: 25
<212> TYPE: PRT
<213> ORGANISM: Pongo pygmaeus

<400> SEQUENCE: 10

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 11

```
<211> LENGTH: 25
<212> TYPE: PRT
<213> ORGANISM: Macaca mulatta

<400> SEQUENCE: 11

Asp Thr His Phe Pro Ile Cys Ile Phe Cys Cys Gly Cys Cys His Arg
1               5                   10                  15

Ser Lys Cys Gly Met Cys Cys Arg Thr
            20                  25

<210> SEQ ID NO 12
<211> LENGTH: 25
<212> TYPE: PRT
<213> ORGANISM: Papio papio

<400> SEQUENCE: 12

Asp Thr His Phe Pro Ile Cys Ile Phe Cys Cys Gly Cys Cys His Arg
1               5                   10                  15

Ser Lys Cys Gly Met Cys Cys Arg Thr
            20                  25

<210> SEQ ID NO 13
<211> LENGTH: 25
<212> TYPE: PRT
<213> ORGANISM: Macaca fascicularis

<400> SEQUENCE: 13

Asp Thr His Phe Pro Ile Cys Ile Phe Cys Cys Gly Cys Cys His Arg
1               5                   10                  15

Ser Lys Cys Gly Met Cys Cys Arg Thr
            20                  25

<210> SEQ ID NO 14
<211> LENGTH: 25
<212> TYPE: PRT
<213> ORGANISM: Chlorocebus aethiops

<400> SEQUENCE: 14

Asp Thr His Phe Pro Ile Cys Ile Phe Cys Cys Gly Cys Cys His Arg
1               5                   10                  15

Ser Lys Cys Gly Met Cys Cys Arg Thr
            20                  25

<210> SEQ ID NO 15
<211> LENGTH: 25
<212> TYPE: PRT
<213> ORGANISM: Macaca fuscata

<400> SEQUENCE: 15

Asp Thr His Phe Pro Ile Cys Ile Phe Cys Cys Gly Cys Cys His Arg
1               5                   10                  15

Ser Lys Cys Gly Met Cys Cys Arg Thr
            20                  25

<210> SEQ ID NO 16
<211> LENGTH: 25
<212> TYPE: PRT
<213> ORGANISM: Pongo abelii

<400> SEQUENCE: 16

Asp Thr His Phe Pro Ile Tyr Ile Phe Cys Cys Gly Cys Cys His Arg
1               5                   10                  15
```

```
Ser Lys Cys Gly Met Cys Cys Lys Thr
        20                  25

<210> SEQ ID NO 17
<211> LENGTH: 25
<212> TYPE: PRT
<213> ORGANISM: Nomascus concolor

<400> SEQUENCE: 17

Asp Thr His Phe Pro Ile Cys Ile Phe Cys Cys Gly Cys Cys His Arg
1               5                   10                  15

Ser Lys Cys Gly Met Cys Cys Lys Thr
        20                  25

<210> SEQ ID NO 18
<211> LENGTH: 25
<212> TYPE: PRT
<213> ORGANISM: Hylobates lar

<400> SEQUENCE: 18

Asp Thr His Phe Pro Ile Cys Ile Phe Cys Cys Gly Cys Cys His Arg
1               5                   10                  15

Ser Lys Cys Gly Met Cys Cys Lys Thr
        20                  25

<210> SEQ ID NO 19
<211> LENGTH: 25
<212> TYPE: PRT
<213> ORGANISM: Callithrix jacchus

<400> SEQUENCE: 19

Asp Thr His Phe Pro Ile Cys Ile Phe Cys Cys Gly Cys Cys Arg Gln
1               5                   10                  15

Ser Asn Cys Gly Met Cys Cys Lys Thr
        20                  25

<210> SEQ ID NO 20
<211> LENGTH: 25
<212> TYPE: PRT
<213> ORGANISM: Ateles fusciceps

<400> SEQUENCE: 20

Asp Thr His Phe Pro Ile Cys Ile Phe Cys Cys Gly Cys Cys Arg Gln
1               5                   10                  15

Pro Asn Cys Gly Met Cys Cys Lys Thr
        20                  25

<210> SEQ ID NO 21
<211> LENGTH: 25
<212> TYPE: PRT
<213> ORGANISM: Bubalus bubalis

<400> SEQUENCE: 21

Asp Thr His Phe Pro Ile Cys Ile Phe Cys Cys Gly Cys Cys Arg Lys
1               5                   10                  15

Gly Thr Cys Gly Met Cys Cys Arg Thr
        20                  25

<210> SEQ ID NO 22
<211> LENGTH: 25
<212> TYPE: PRT
<213> ORGANISM: Bos taurus
```

```
<400> SEQUENCE: 22

Asp Thr His Phe Pro Ile Cys Ile Phe Cys Cys Gly Cys Cys Arg Lys
1               5                   10                  15

Gly Thr Cys Gly Met Cys Cys Arg Thr
            20                  25

<210> SEQ ID NO 23
<211> LENGTH: 25
<212> TYPE: PRT
<213> ORGANISM: Bos grunniens

<400> SEQUENCE: 23

Asp Thr His Phe Pro Ile Cys Ile Phe Cys Cys Gly Cys Cys Arg Lys
1               5                   10                  15

Gly Thr Cys Gly Met Cys Cys Arg Thr
            20                  25

<210> SEQ ID NO 24
<211> LENGTH: 25
<212> TYPE: PRT
<213> ORGANISM: Canis lupus familiaris

<400> SEQUENCE: 24

Asp Thr His Phe Pro Ile Cys Ile Phe Cys Cys Gly Cys Cys Lys Thr
1               5                   10                  15

Pro Lys Cys Gly Leu Cys Cys Lys Thr
            20                  25

<210> SEQ ID NO 25
<211> LENGTH: 25
<212> TYPE: PRT
<213> ORGANISM: Sus scrofa

<400> SEQUENCE: 25

Asp Thr His Phe Pro Ile Cys Ile Phe Cys Cys Gly Cys Cys Arg Lys
1               5                   10                  15

Ala Ile Cys Gly Met Cys Cys Lys Thr
            20                  25

<210> SEQ ID NO 26
<211> LENGTH: 25
<212> TYPE: PRT
<213> ORGANISM: Canis lupus familiaris

<400> SEQUENCE: 26

Asp Thr His Phe Pro Ile Cys Ile Phe Cys Cys Gly Cys Cys Lys Thr
1               5                   10                  15

Pro Lys Cys Gly Phe Cys Cys Lys Thr
            20                  25

<210> SEQ ID NO 27
<211> LENGTH: 25
<212> TYPE: PRT
<213> ORGANISM: Equus caballus

<400> SEQUENCE: 27

Asp Thr His Phe Pro Ile Cys Thr Leu Cys Cys Gly Cys Cys Asn Lys
1               5                   10                  15

Gln Lys Cys Gly Trp Cys Cys Lys Thr
            20                  25
```

```
<210> SEQ ID NO 28
<211> LENGTH: 25
<212> TYPE: PRT
<213> ORGANISM: Mus musculus

<400> SEQUENCE: 28

Asp Thr Asn Phe Pro Ile Cys Ile Phe Cys Cys Lys Cys Cys Asn Asn
1               5                   10                  15

Ser Gln Cys Gly Ile Cys Cys Lys Thr
            20                  25

<210> SEQ ID NO 29
<211> LENGTH: 25
<212> TYPE: PRT
<213> ORGANISM: Rattus norvegicus

<400> SEQUENCE: 29

Asp Thr Asn Phe Pro Ile Cys Leu Phe Cys Cys Lys Cys Cys Lys Asn
1               5                   10                  15

Ser Ser Cys Gly Leu Cys Cys Ile Thr
            20                  25

<210> SEQ ID NO 30
<211> LENGTH: 26
<212> TYPE: PRT
<213> ORGANISM: Mus musculus

<400> SEQUENCE: 30

Met Asp Ile Asn Phe Pro Ile Cys Arg Phe Cys Cys Gln Cys Cys Asn
1               5                   10                  15

Lys Pro Ser Cys Gly Ile Cys Cys Glu Glu
            20                  25

<210> SEQ ID NO 31
<211> LENGTH: 25
<212> TYPE: PRT
<213> ORGANISM: Xenopus (Silurana) tropicalis

<400> SEQUENCE: 31

Arg His Leu Asn Ile Cys Val Tyr Cys Cys Lys Cys Cys Lys Lys Gln
1               5                   10                  15

Lys Gly Cys Gly Met Cys Cys Phe Thr
            20                  25

<210> SEQ ID NO 32
<211> LENGTH: 25
<212> TYPE: PRT
<213> ORGANISM: Paralichthys olivaceus

<400> SEQUENCE: 32

Ile Ser His Ile Ser Met Cys Arg Trp Cys Cys Asn Cys Cys Lys Ala
1               5                   10                  15

Lys Gly Cys Gly Pro Cys Cys Lys Phe
            20                  25

<210> SEQ ID NO 33
<211> LENGTH: 25
<212> TYPE: PRT
<213> ORGANISM: Danio rerio

<400> SEQUENCE: 33

Gln Ser His Leu Ser Leu Cys Arg Phe Cys Cys Lys Cys Cys Arg Asn
1               5                   10                  15
```

```
Lys Gly Cys Gly Tyr Cys Cys Lys Phe
            20                  25

<210> SEQ ID NO 34
<211> LENGTH: 26
<212> TYPE: PRT
<213> ORGANISM: Gadus morhua

<400> SEQUENCE: 34

Gln Ser His Leu Ala Leu Cys Arg Trp Cys Cys Asn Cys Cys Arg Asn
1               5                   10                  15

Gln Lys Gly Cys Gly Ile Cys Cys Lys Phe
            20                  25
```

TREATMENT OF OSTEOPOROSIS IN PERI- AND POST-MENOPAUSAL WOMEN WITH HEPCIDIN

This application claims the benefit of U.S. Provisional Patent Application Ser. No. 61/151,648, filed Feb. 11, 2009, which is hereby incorporated by reference in its entirety.

FIELD OF THE INVENTION

The present invention is related to the treatment of osteoporosis in peri- or post-menopausal women with hepcidin.

BACKGROUND OF THE INVENTION

Osteoporosis is the most common form of metabolic bone disease. It is a chronic disease characterized by low bone mineral density (BMD), which results in a high incidence of bone fractures, especially of the hip. The mechanism by which bone is lost in osteoporotics is believed to be the imbalance in the process by which the skeleton renews itself. In a healthy adult, there is a balance between the rates of bone formation and bone resorption.

Post-menopausal women are particularly at risk to imbalances in the rates of bone formation and resorption and likely to develop idiopathic osteoporosis ("post-menopausal osteoporosis"). Post-menopausal osteoporosis occurs in about 50% of women over 50 years of age and those who suffer from hip fracture become dependent on others for daily activities (Ray et al., "Medical Expenditures for the Treatment of Osteoporotic Fractures in the United States in 1995: Report from the National Osteoporosis Foundation," *J. Bone Miner. Res.* 12:24-35 (1997); Ross P. D., "Osteoporosis. Frequency, Consequences, and Risk Factors," *Arch. Intern. Med.* 156:1399-411 (1996)). In the United States alone, the cost—both direct (i.e. hospitalization, surgery, doctor's visits) and indirect (i.e. loss time from work)—from factures exceeds $7 billion annually.

Several risk factors have been identified in relation to osteoporosis: genetic predisposition, sedentary lifestyle, low dietary intake of calcium and vitamin D, physical activity, petite stature and small bone fracture, long-term use of steroids or heparin, cigarette smoking, and declining levels of estrogen after menopause (Society NAM, "Management of Osteoporosis in Post-Menopausal Women: 2006 Position Statement of the North American Menopause Society," *Menopause* 13:340-367 (2006)). Estrogen deficiency is considered one of the most important risk factors (Choo et al., "Osteoporosis in Relation to Menopause," *Ann. Acad. Med. Singapore* 31:30-6 (2002); Kanis J. A., "Estrogens, the Menopause, and Osteoporosis," *Bone* 19 (5 Suppl.):185S-190S (1996)), because bone loss accelerates 2-3 years after menopause at a rate of 1-1.5% annually (Recker et al., "Characterization of Peri-menopausal Bone Loss: a Prospective Study," *J. Bone Miner. Res.* 15:1965-73 (2000)). Hormone replacement therapy (HRT) is partially effective in slowing down bone loss in post-menopausal women (Ravn et al., "Alendronate and Estrogen-progestin in the Long-term Prevention of Bone Loss: Four-year Results from the Early Post-menopausal Intervention Cohort Study. A Randomized, Controlled Trial," *Ann. Intern. Med.* 131:935-42 (1999)). The partial alleviation of HRT also suggests that factors other than estrogen may play an important role in post-menopausal osteoporosis (Society NAM, "Management of Osteoporosis in Post-menopausal Women: 2006 Position Statement of The North American Menopause Society," *Menopause* 13:340-367 (2006)).

A number of treatments have been suggested for osteoporosis. Most agents used to treat osteoporosis, such as hormones, parathyroids, bisphosphonates, are not very effective and these treatments cause significant side effects, e.g. osteonecrosis caused by bisphosphonates (Grewal et al. "Bisphosphonate-associated Osteonecrosis: A Clinician's Reference to Patient Management," *Todays FDA* 20:38-41, 43-6 (2008)).

Thus, there is a need in the art for a safe and effective way of treating, preventing, or reducing the risk of bone deterioration or osteoporosis, particularly in peri- or post-menopausal women.

The present invention is directed to overcoming these and other deficiencies in the art.

SUMMARY OF THE INVENTION

One aspect of the present invention relates to a method of treating, preventing, or reducing the risk of bone deterioration or osteoporosis in a peri- or post-menopausal female subject. This method involves selecting a peri- or post-menopausal female subject in need of treating, preventing, or reducing the risk of bone deterioration or osteoporosis and administering hepcidin to the selected subject under conditions effective to treat, prevent, or reduce the risk of bone deterioration or osteoporosis.

Applicants have observed that serum iron and ferritin levels are significantly higher in post-menopausal women than in pre-menopausal women. To study the cause of this increase in iron, all the three stages of the life of an adult woman according to the menopausal status have been investigated.

As shown in FIG. 1, pre-menopause starts from the first menstrual period to the beginning of peri-menopause at the age of approximately 42. Through a complex interaction of hypothalamic-pituitary-ovarian (HPO) glands, the pituitary gland stimulates the ovaries to mature and release an egg every month (Genazzani et al., "Endocrinology of Menopausal Transition and its Brain Implications," *CNS Spectr.* 10:449-57 (2005); Prior J. C., "Ovarian Aging and the Perimenopausal Transition: the Paradox of Endogenous Ovarian Hyperstimulation," *Endocrine* 26:297-300 (2005), which are hereby incorporated by reference in their entirety). When the egg is not fertilized, endometrial matrix prepared for egg fertilization is shed in the form of blood. Therefore, in young, pre-menopausal women, estrogen levels are high and iron levels are low.

As a woman matures and enters menopausal transition, the ovaries have fewer eggs to stimulate. Women at this stage are characterized by an irregular menstrual cycle and prolonged days of amenorrhea (days without menstruation). During menopausal transition, inverse but concurrent changes in levels of estrogen (Estradiol, E2) and iron (Ferritin) occur as shown in FIG. 2. The menopausal transition concludes with the final menstrual cycle and the beginning of post-menopause at an average age of 51 years old.

Post-menopause begins at the time of the final menstrual period and is usually recognized after 12 months of amenorrhea. The dynamics of the HPO hormones change dramatically from cyclic to static patterns and serum levels of estrogen significantly diminish (Bellino F. L., *Biology of Menopause*, (2000); Bellino et al., "Nonhuman Primate Models of Menopause Workshop," *Biol. Reprod.* 68:10-18. (2003), which are hereby incorporated by reference in their entirety). Women entering menopausal transition not only experience a decrease in estrogen, which is widely recognized by the medical professionals, but also an increase in iron, which has never been explored in relation to menopausal symptoms and diseases. Therefore, in older, post-menopausal women, reverses are true: low estrogen and high iron.

Many women experience menopausal symptoms such as vasomotor episodes or "hot flashes" as well as patho-physiological conditions such as loss of bone mineral density (Nelson H. D., "Menopause," *Lancet* 371:760-70 (2008), which is hereby incorporated by reference in its entirety). Estrogen replacement has been the main medical treatment to increase body estrogen and partially improve the symptoms.

Estrogen and iron are two of the most important growth nutrients in a female body development. Estrogen influences the growth, differentiation, and function of tissues of the female reproductive system, i.e., uterus, ovary, and breast (Zhu et al., "Functional Role of Estrogen Metabolism in Target Cells: Review and Perspectives," *Carcinogenesis* 19:1-27 (1998), which is hereby incorporated by reference in its entirety). Iron, like estrogen, is essential for cell growth and metabolic processes, including oxygen transport, enzyme functions, DNA synthesis, and electron transport. However, too much iron can lead to adverse health effects, such as producing oxidants and oxidative stress, which could cause organ damages. For example, ferritin (Ftn), an iron storage protein with a capacity of binding up to 4500 atoms of iron, is increased 2-3 fold during the menopausal transition. Iron transported by transferrin, which has two binding sites for iron, also known as serum iron, is significantly increased in the same period. Whether this increase in body iron contributes to menopausal symptoms and diseases has not been known.

The method of the present invention permits treating, preventing, or reducing the risk of bone deterioration or osteoporosis in peri- or post-menopausal women through regulation of iron. It has been demonstrated that increased iron inhibits bone formation and thereby affects the balance between bone formation and bone resorption. Further, increased iron is a risk factor that is independent of estrogen deficiency in menopausal symptoms and disease. Accordingly, the present invention proposes the use of hepcidin to control the increased iron concentration due to menopause in women and thus treats, prevents, or reduces the risk of bone deterioration or osteoporosis.

DETAILED DESCRIPTION OF THE INVENTION

Figure 1:
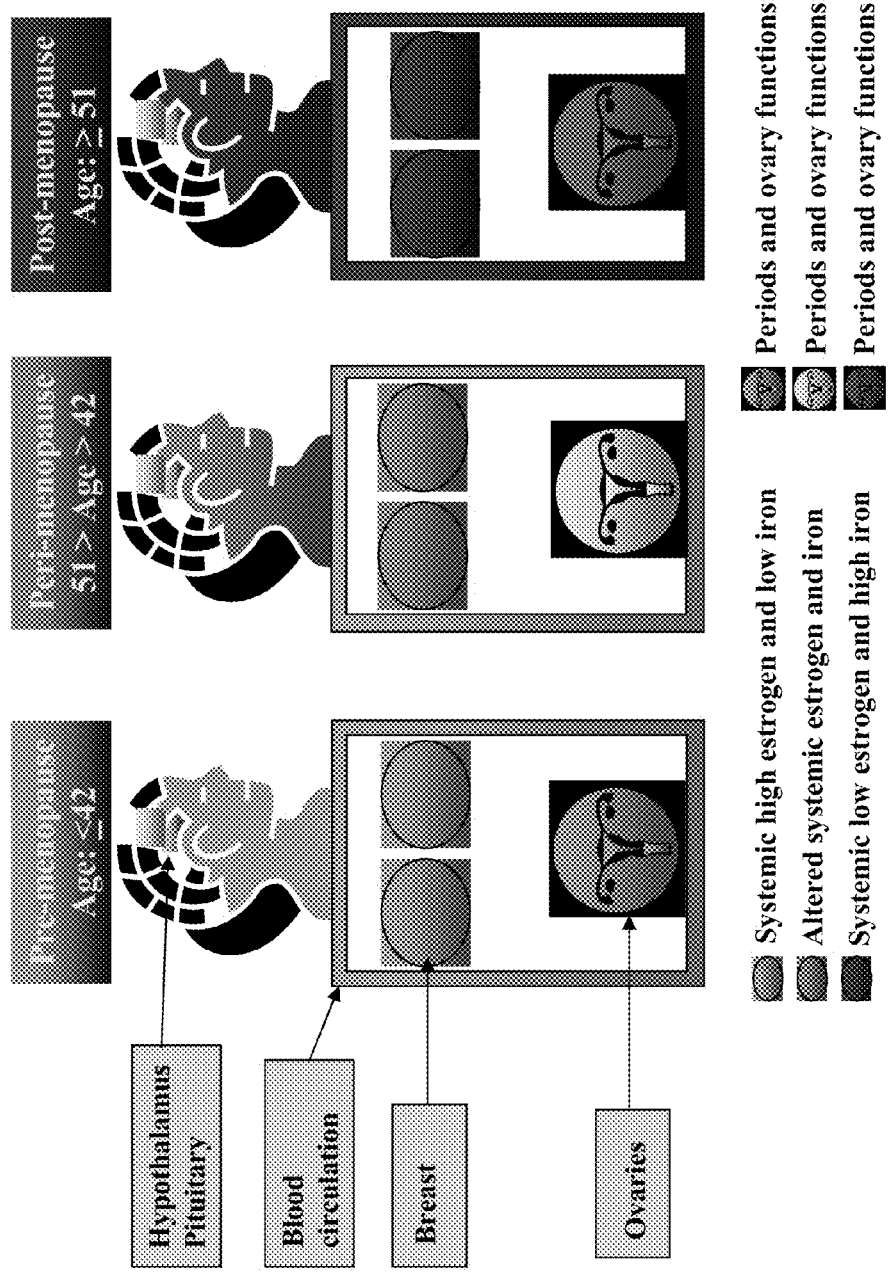
FIG. 1 depicts the menopausal status across the lifespan of a woman and the regulation of ovary function and menstrual periods by the hypothalamus-pituitary-ovary (HPO) glands.
Figure 2:
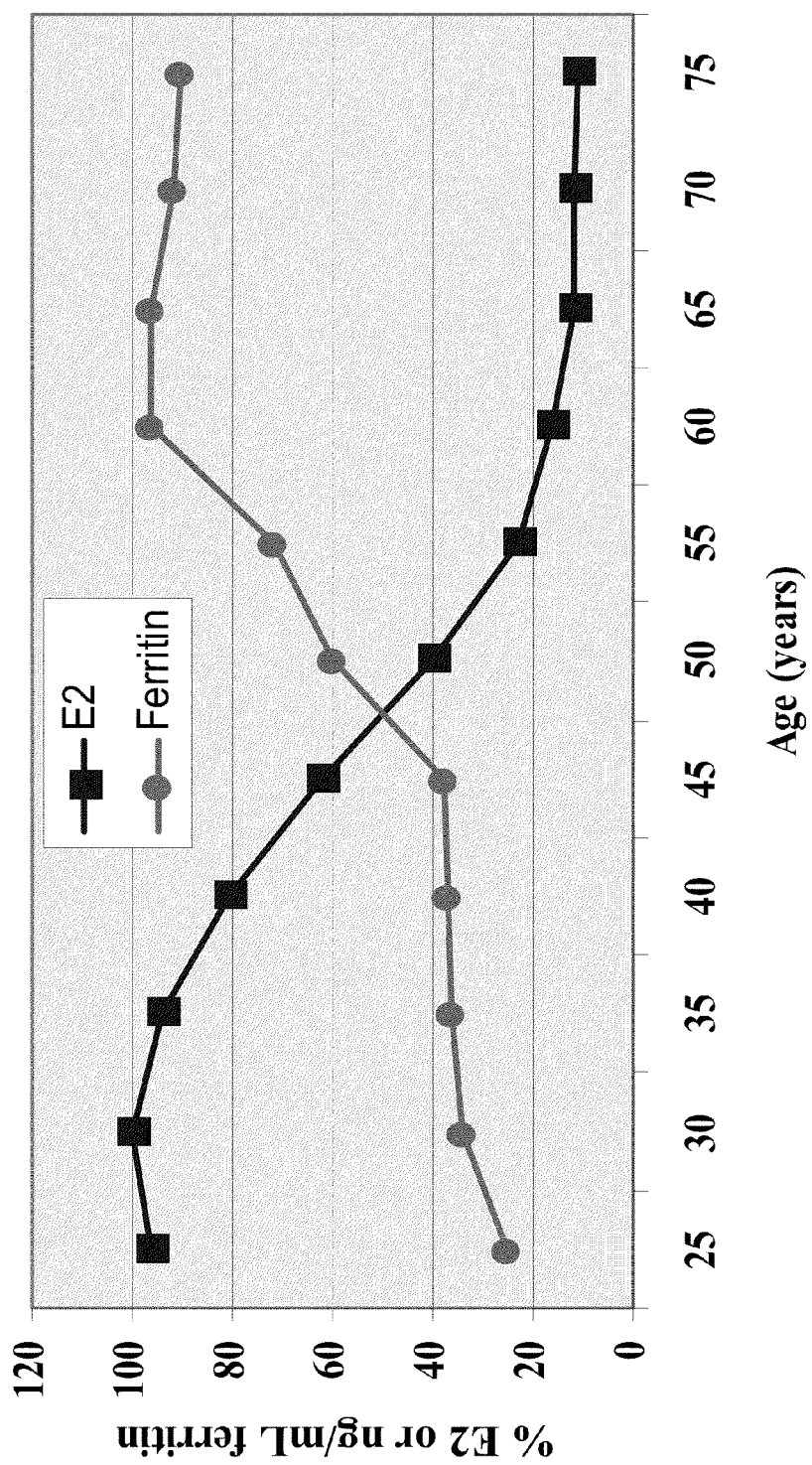
FIG. 2 depicts concurrent but inverse changes in E2 (estradiol, estrogen) and ferritin (iron levels) during menopausal transition. Serum levels of 17β-estradiol (E2) were converted to % of peak value at 500 pg/ml serum at age 25. Levels of ferritin were expressed in ng/ml serum.

The present invention relates to a method of treating, preventing, or reducing the risk of bone deterioration or osteoporosis in a peri- or post-menopausal female subject. The method involves selecting a peri- or post-menopausal female subject in need of treating, preventing, or reducing the risk of bone deterioration or osteoporosis and administering hepcidin to the selected subject under conditions effective to treat, prevent, or reduce the risk of bone deterioration or osteoporosis.

A bone deterioration condition generally refers to a condition where the quality of bone deteriorates such that the tendency of bone to acquire structural defects or to fracture increases. Examples of such conditions include: deterioration of the trabecular or bone architecture, decrease in calcium bioavailability, decrease in bone calcification rates, decrease in bone formation rates, decrease in osteoblast proliferation rates, decrease in differentiation rate of osteoblasts, and osteopoenia.

The subject treated according to method of the present invention can be any animal that exhibits menopause related bone deterioration or osteoporosis, preferably a mammalian subject. Exemplary mammalian subjects include, without limitation, humans, non-human primates, dogs, cats, rodents (e.g., mouse, rat, guinea pig), horses, cattle and cows, sheep, and pigs.

Hepcidin, is a peptide hormone and is the principal regulator of iron homeostasis (Ganz et al. "Hepcidin: A Regulator of Intestinal Iron Absorption and Iron Recycling by Macrophages," *Best Pract. Res. Clin. Haematol.* 18:171-182 (2005), which is hereby incorporated by reference in its entirety). Iron homeostasis is regulated in the body primarily through regulation of dietary iron capture by the intestine and by iron recycling by macrophages. Hepcidin is the key signal peptide regulating iron homeostasis (Collins et al., "Hepcidin Regulation of Iron Transport," *J Nutr* 138, 2284-8 (2008), which is hereby incorporated by reference in its entirety). High levels of hepcidin reduce body iron levels, and vice versa. Ferroportin is a major iron export protein, which is located on the cell surface of enterocytes. Hepcidin binds to ferroportin and decreases its functional activity by causing ferroportin internalization and, thus, inhibiting iron uptake and transfer from gastrointestinal system to the circulating system (Nemeth, E. et al., "Hepcidin Regulates Iron Efflux by Binding to Ferroportin and Inducing Its Internalization," *Science* 306:2090-3 (2004), which is hereby incorporated by reference in its entirety). The active form of hepcidin contains eight cysteine residues linked as four disulfide bridges. It has been shown that mice receiving a single 50 µg intraperitoneal injection of human hepcidin caused a 70% fall in serum iron for 3 days (Rivera, S. et al., "Synthetic Hepcidin Causes Rapid Dose-dependent Hypoferremia and Is Concentrated in Ferroportin-containing Organs," *Blood* 106, 2196-9 (2005), which is hereby incorporated by reference in its entirety). Since increased iron is responsible for decreasing bone formation, leading to the development of osteoporosis, hepcidin treatment will at least prevent bone loss caused by iron and, thus, promote an increase in bone mass. Moreover, hepcidin treatment could also decrease estrogen metabolism to its carcinogenic compounds and increase half life of the good bone-benefiting 17β-estradiol (E2).

Hepcidin acts by binding to ferroportin (the sole cellular exporter of iron) and inducing its internalization and degradation (Nemeth et al. "Hepcidin Regulates Cellular Iron Efflux by Binding to Ferroportin and Inducing its Internalization," *Science* 306:2090-2093 (2005), which is hereby incorporated by reference in its entirety). Hepcidin production increases with iron loading and inflammation, anemia, and hypoxia lead to a decrease in hepcidin production (Pigeon et al. "A New Mouse Liver Specific Gene, Encoding a Protein Homologous to Human Antimicrobial Peptide Hepcidin, is Overexpressed During Iron Overload," *J. Biol. Chem.* 276:7811-7819 (2001); Nicolas et al. "The Gene Encoding the Iron Regulatory Peptide Hepcidin is Regulated by Anemia, Hypoxia, and Inflammation," *J. Clin. Invest.* 110: 1037-1044 (2002), which are hereby incorporated by reference in their entirety). Hepcidin (also referred as LEAP-1, for Liver-Expressed Antimicrobial Peptide) was purified from human blood and from urine. It is predominantly synthesized in liver and exhibits antimicrobial activity.

The protein is synthesized in liver as a proprehepcidin that contains 84 amino acid residues with a signal peptide and a consensus cleavage site for a prohormone convertase that generates the mature bioactive 25-amino acid peptide form found in plasma and urine. The human urine also has 20- and 22-amino acid forms of the mature bioactive peptide truncated at the N-terminus (Krause et al. "LEAP-1 a Novel Highly Disulfide-bonded Human Peptide, Exhibits Antimicrobial Activity," *FEBS Lett.* 480:147-150 (2000); Park et al. "Hepcidin, a Urinary Antimicrobial Peptide Synthesized in the Liver," *J. Biol. Chem.* 276:7806-7810 (2001), which are hereby incorporated by reference in their entirety). The truncated forms of mature bioactive hepcidin display much reduced iron regulatory activity (Nemeth et al., "The N-terminus of Hepcidin is Essential for its Interaction with Ferroportin: Structure-function study," *Blood* 107:328-33 (2005); Rivera et al, "Synthetic Hepcidin Causes Rapid Dose Dependent Hypoferremia and is Concentrated in Ferroportin-containing Organs," *Blood* 105:1797-1802 (2005), which are hereby incorporated by reference in their entirety). The 25 amino acid hepcidin peptide forms a hairpin loop stabilized by 4 disulfide bonds (Hunter et al. "The Solution Structure of Human Hepcidin, a Peptide Hormone with Antimicrobial Activity that is Involved in Iron Uptake and Hereditary Hemochromatosis," *J. Biol. Chem.* 277:37597-37603 (2002), which is hereby incorporated by reference in its entirety). Three dimensional nuclear magnetic resonance studies of hepcidin show that it is an amphipathic peptide similar to many antimicrobial peptides. Hepcidin sequence is conserved across species, ranging from fish to mammals (Shike et al., "Organization and Expression Analysis of the Zebrafish Hepcidin Gene, an Antimicrobial Peptide Gene Conserved among Vertebrates," *Dev. Comp. Immunol.* 28:747-754 (2004), which is hereby incorporated by reference in its entirety).

The hepcidin can be administered as a polypeptide having the amino acid sequence of SEQ ID NO. 1 as follows:

(SEQ ID NO: 1)
$Xaa^1-Xaa^2-Xaa^3-Xaa^4-Xaa^5-Xaa^6-Xaa^7-Xaa^8-Xaa^9-$
$Cys^{10}-Cys^{11}-Xaa^{12}-Cys^{13}-Cys^{14}-Xaa^{15}-Xaa^{16}-Xaa^{17}-$
$Xaa^{18}-Cys^{19}-Gly^{20}-Xaa^{21}-Cys^{22}-Xaa^{23}-Xaa^{24}-Xaa^{25}$, $Xaa^1$ is Asp, Gln or absent,
$Xaa^2$ is Thr, Ile, Ser or absent,
$Xaa^3$ is Asn, His or absent,
$Xaa^4$ is Phe, Leucine or absent,
$Xaa^5$ is Pro, Ser or absent,
$Xaa^6$ is Leu or Ile,
$Xaa^7$ is Cys, Ala, or Tyr,
$Xaa^8$ is Ile, Leu, Thr or Arg,
$Xaa^9$ is Phe or Leu,
$Xaa^{12}$ is Lys, Gly, Asp or Gln,
$Xaa^{15}$ is Asn, His, Arg or Lys,
$Xaa^{16}$ is Asn, Thr, Gln, Lys or Arg,
$Xaa^{17}$ is Pro, Gln, Ser, Ala, Lys or Gly,
$Xaa^{18}$ is Gln, Gly, Ser, Lys, Asn, Thr, or Ile,
$Xaa^{21}$ is Ile, Leu, Phe, Tyr, Met or Trp,
$Xaa^{23}$ is Cys or Ala,
$Xaa^{24}$ is Lys, Ile, Arg, Glu or absent,
$Xaa^{25}$ is Thr, Phe, Glu or absent.

Figure 3:
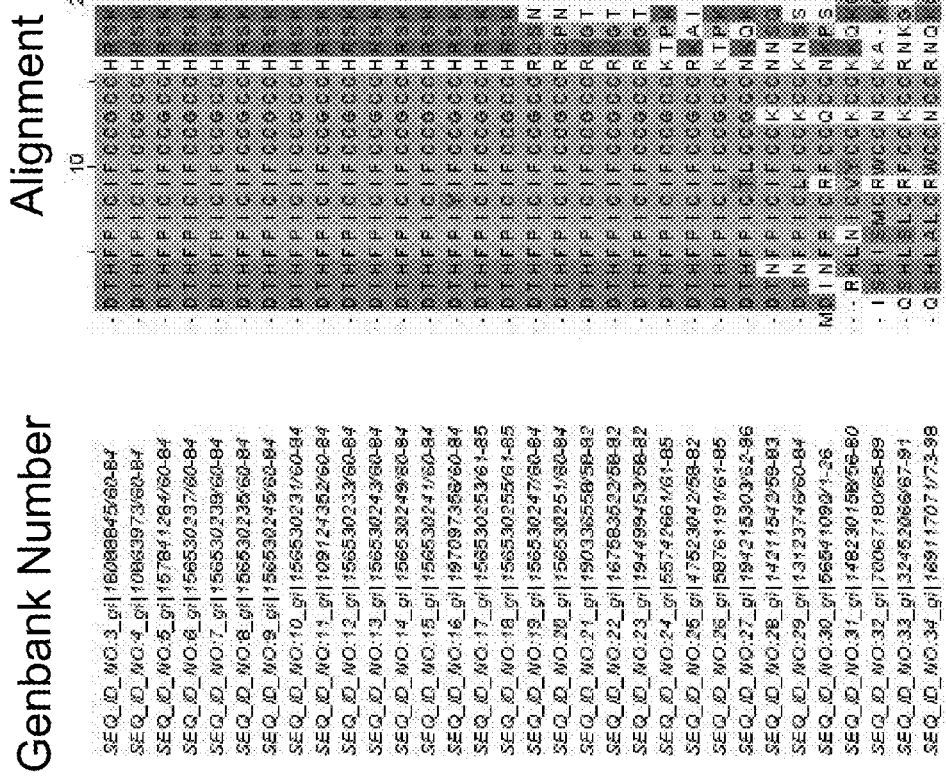
FIG. 3 shows the sequence alignment for hepcidin polypeptide sequences (SEQ ID NOs: 3-34) obtained from GenBank. Amino acid residues are indicated using single letter designation. GenBank accession numbers and the residue numbers selected for alignment are listed before the sequences. Same color columns show conserved sequences among the aligned sequences.

This generalized amino acid sequence encompasses a number of natural and synthetic polypeptides. These also include hepcidin sequences listed on GenBank, for example sequences with the following GenBank Accession numbers: gi|18088845, gi|10863973, gi|157841284, gi|156530237, gi|156530239, gi|156530235, gi|156530245, gi|156530231, gi|109124352, gi|156530233, gi|156530243, gi|156530249, gi|156530241, gi|197097356, gi|156530253, gi|156530255, gi|156530247, gi|156530251, gi|190336558, gi|167583522, gi|194499453, gi|55742661, gi|47523042, gi|58761191, gi|194215303, gi|14211542, gi|13123746, gi|56541090, gi|148230158, gi|70067180, gi|32452066, gi|169117071. FIG. 3 shows alignment of these sequences. Of the known hepcidin polypeptides it is particularly desirable to utilize human hepcidin. Human hepcidin has the following amino acid sequence (SEQ ID NO. 2):

$Asp^1-Thr^2-His^3-Phe^4-Pro^5-Ile^6-Cys^7-Ile^8-Phe^9-$
$Cys^{10}-Cys^{11}-Gly^{12}-Cys^{13}-Cys^{14}-His^{15}-Arg^{16}-Ser^{17}-$
$Lys^{18}-Cys^{19}-Gly^{20}-Met^{21}-Cys^{22}-Cys^{23}-Lys^{24}-Thr^{25}$.

The invention also encompasses the use of functional equivalents of the above-defined polypeptides. Functional equivalents are herein defined as peptide variants, or other compounds having the same functional activity as the mature forms of hepcidin. Examples of such functional equivalents include chemical compounds which are modeled to mimic the three dimensional structure of a hepcidin. Of particular interest are derivatives of such polypeptides having an improved stability and biological half life. Classical examples of such derivatives are for instance "retro-inverso" peptides, wherein the sequence of the amino-acids is reversed, and the L-amino acids are replaced with D-amino acids. Another example of functional equivalents include hepcidin variants that retain the same or similar disulfide connectivity as human hepcidin and that are useful as modulators of hepcidin biological activity. For example, molecules that bind to and activate hepcidin receptor or molecules that bind to and cause internalization of ferroportin can be used.

An alternative approach for delivery of hepcidin involves conjugation of the desired protein or polypeptide to a polymer that is stabilized to avoid enzymatic degradation of the conjugated protein or polypeptide. Conjugated proteins or polypeptides of this type are described in U.S. Pat. No. 5,681,811 to Ekwuribe, which is hereby incorporated by reference in its entirety.

Yet another approach for delivery of proteins or polypeptide agents of the present invention involves preparation of chimeric proteins according to U.S. Pat. No. 5,817,789 to Heartlein et al., which is hereby incorporated by reference in its entirety. The chimeric protein can include a ligand domain and hepcidin. The ligand domain is specific for receptors located on a target cell. Thus, when the chimeric protein is delivered intravenously or otherwise introduced into blood or lymph, the chimeric protein will adsorb specifically to the targeted cell, and the targeted cell will internalize the chimeric protein.

Besides administering hepcidin as a polypeptide, it can be administered in the form of a nucleic acid molecule encoding a hepcidin polypeptide, such as that having the amino acid sequence of SEQ ID NO:1 or SEQ ID NO:2.

Nucleic acid agents (including RNA and DNA) for use in the methods of the present invention can be delivered to a subject in a number of ways known in the art, including through the use of gene therapy vectors. The nucleic acid can be contained within a vector useful for gene therapy, for example, a vector that can be transferred to the cells of a subject and provide for expression of the therapeutic nucleic acid agent therein. Such vectors include chromosomal vectors (e.g., artificial chromosomes), non-chromosomal vectors, and synthetic nucleic acids.

The nucleic acid agents include, operatively coupled to one another, an upstream promoter operable in mammalian cells and optionally other suitable regulatory elements (i.e., enhancer or inducer elements), a coding sequence that encodes the therapeutic nucleic acid (described above), and a downstream transcription termination region. Any suitable constitutive promoter or inducible promoter can be used to regulate transcription of the recombinant gene, and one of skill in the art can readily select and utilize such promoters, whether now known or hereafter developed. Known recombinant techniques can be utilized to prepare the recombinant gene and transfer it into the expression vector. Exemplary procedures are described in JOSEPH SAMBROOK et al., 1-3 MOLECULAR CLONING: A LABORATORY MANUAL (2d ed. 1989), which is hereby incorporated by reference in its entirety. One of skill in the art can readily modify these procedures, as desired, using known variations of the procedures described therein.

Any suitable viral or infective transformation vector can be used. Exemplary viral vectors include, without limitation, adenovirus, adeno-associated virus, and retroviral vectors (including lentiviral vectors).

Adenovirus gene delivery vehicles can be readily prepared and utilized given the disclosure provided in Berkner, "Development of Adenovirus Vectors for the Expression of Heterologous Genes," *Biotechniques* 6:616-29 (1988); Rosenfeld et al., "Adenovirus-mediated Transfer of a Recombinant α1-Antitrypsin Gene to the Lung Epithelium in Vivo," *Science* 252:431-434 (1991); WO 1993/007283 to Curiel et al.; WO 1993/006223 to Perricaudet et al.; and WO 1993/007282 to Curiel et al., which are hereby incorporated by reference in their entirety. Additional types of adenovirus vectors are described in U.S. Pat. No. 6,057,155 to Wickham et al., U.S. Pat. No. 6,033,908 to Bout et al., U.S. Pat. No. 6,001,557 to Wilson et al., U.S. Pat. No. 5,994,132 to Chamberlain et al., U.S. Pat. No. 5,981,225 to Kochanek et al., U.S. Pat. No. 5,885,808 to Spooner et al., and U.S. Pat. No. 5,871,727 to Curiel, which are hereby incorporated by reference in their entirety.

Adeno-associated viral gene delivery vehicles can be constructed and used to deliver into cells a recombinant gene encoding a desired nucleic acid. The use of adeno-associated viral gene delivery vehicles in vivo is described in Flotte et al., "Stable in Vivo Expression of the Cystic Fibrosis Transmembrane Conductance Regulator with an Adeno-associated Virus Vector," *Proc. Nat'l Acad. Sci. USA* 90:10613-7 (1993), and Kaplitt et al., "Long-term Gene Expression and Phenotypic Correction Using Adeno-associated Virus Vectors in the Mammalian Brain," *Nat. Genet.* 8:148-54 (1994), which are hereby incorporated by reference in their entirety.

Retroviral vectors which have been modified to form infective transformation systems can also be used to deliver a recombinant gene encoding a desired nucleic acid product into a target cell. One such type of retroviral vector is disclosed in U.S. Pat. No. 5,849,586 to Kriegler et al., which is hereby incorporated by reference in its entirety. Lentivirus vectors can also be utilized, including those described in U.S. Pat. No. 6,790,657 to Arya, U.S. Patent Application Publication No. 2004/0170962 to Kafri et al., and U.S. Patent Application Publication No. 2004/0147026 to Arya, which are hereby incorporated by reference in their entirety.

As an alternative to non-infective delivery of nucleic acids as described above, naked DNA or infective transformation vectors can be used for delivery, whereby the naked DNA or infective transformation vector contains a recombinant gene that encodes, for example, the hepcidin polypeptide of the present invention. The nucleic acid molecule is then expressed in transformed cells.

As will be apparent to one of ordinary skill in the art, administering any of the agents of the present invention may be carried out using generally known methods. Typically, the agents of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The active agents of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of active compound. The percentage of the agent in these compositions may, of course, be varied and may conveniently be between about 2% to about 60% of the weight of the unit. The amount of active agent in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

These active agents may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The agents of the present invention may also be administered directly to the airways in the form of an aerosol. For use as aerosols, the agents of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The present invention is illustrated, but not limited, by the following examples.

EXAMPLES

Example 1

Cell Culture Models for Pre- and Post-Menopausal Conditions

Figure 4:
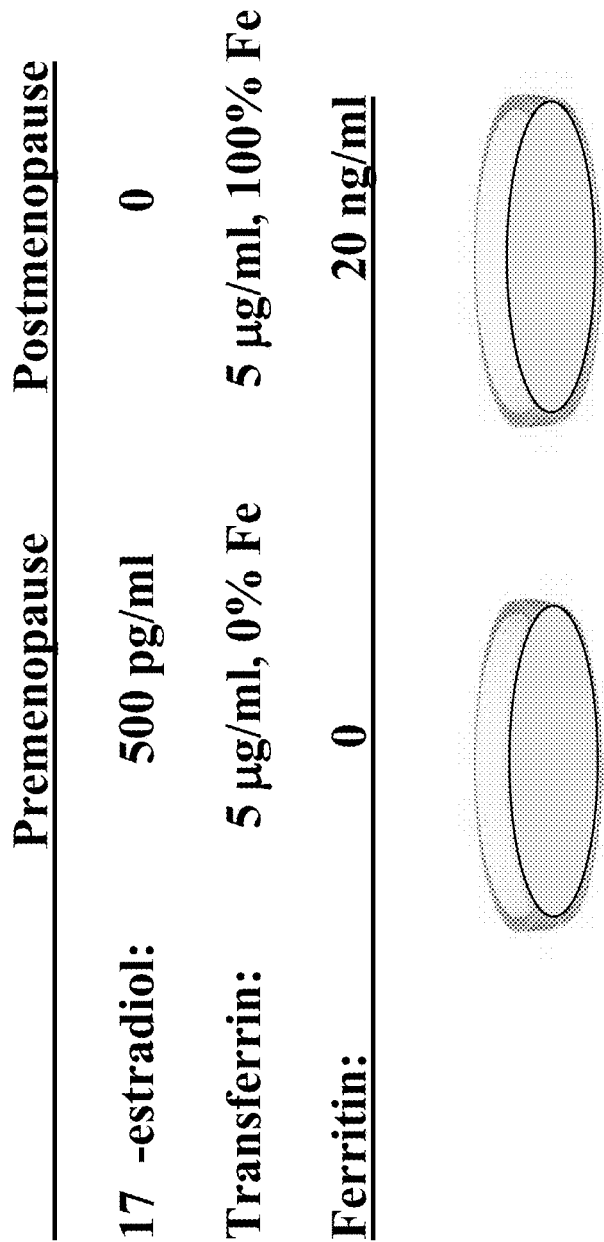
FIG. 4 shows the development of cell culture models mimicking pre- and post-menopausal conditions.

Due to the deficit of appropriate animal models that recapitulate estrogen and iron conditions in vivo, and the inherent difficulty of eliminating confounding variables with study in human subjects, applicants developed two cell culture models to test whether increase in body iron contributes to menopausal symptoms and diseases (FIG. 4). The concentration of 17β-estradiol (E2) were set at levels equivalent to breast tissue levels under pre-menopausal conditions (Parl F. F., "Estrogens, Estrogen Receptor and Breast Cancer," *Oxford: IOS Press*, (2000), which is hereby incorporated by reference in its entirety). Ferritin levels were equal to 10% serum, given that the physiological upper limit of serum ferritin is 200 ng/ml. Twenty ng/ml of ferritin was used in the culture media. Transferrin was added in its wholly unsaturated form (apo-transferrin), or its fully 100% iron saturated (holo-transferrin), at 5 μg/ml, to the pre- and post-menopausal conditions, respectively. Serum-free alpha minimum essential medium (α-MEM) was used as the base medium for breast cancer MCF-7 cells, osteoblast progenitor C2C12 cells, and osteoclast progenitor Raw 264.7 cells. MCF-7 was supplemented with selenium (5 ng/ml) and insulin (5 μg/ml). C2C12 and Raw 264.7 cells were supplemented with bone morphorgenetic protein-2 (BMP-2) and receptor activator of nuclear factor kappa B ligand (RANKL) to stimulate their differentiation and maturation to ostoeblasts and osteoclasts, respectively. Epilife® basal medium was used for the culture of primary normal human epidermal keratinocytes (NHEK) cells.

Example 2

Study on the Effect of Iron Levels on VEGF Formation

Figure 5:
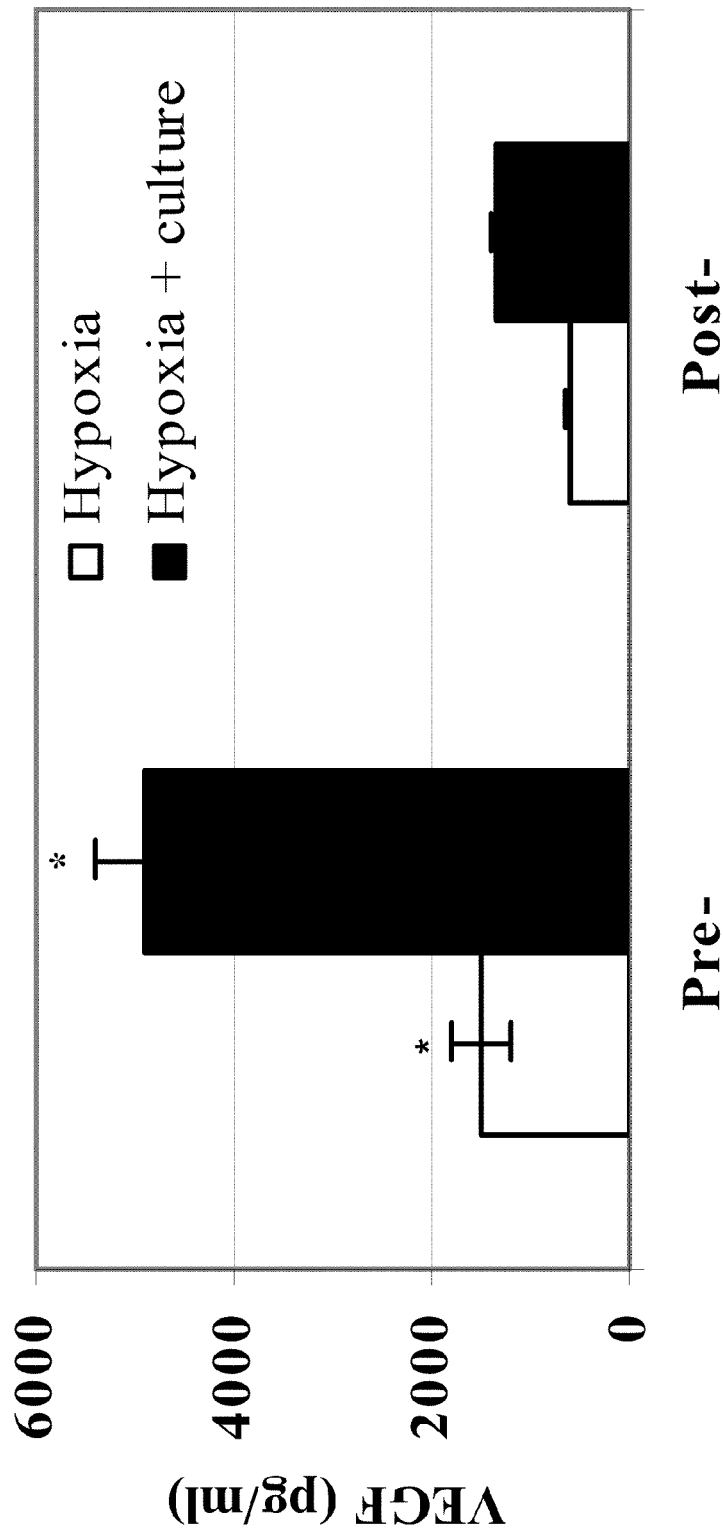
FIG. 5 depicts differences in levels of VEGF between MCF-7 cells grown under pre- (high E2 and low Fe) and post-menopausal (low E2 and high Fe) conditions after exposure to 1% $O_2$ for 6 h, followed by overnight culture under normoxia (hypoxia+culture). * indicates a significant difference from cells grown under post-menopausal conditions by Student's t test.
Figure 6:
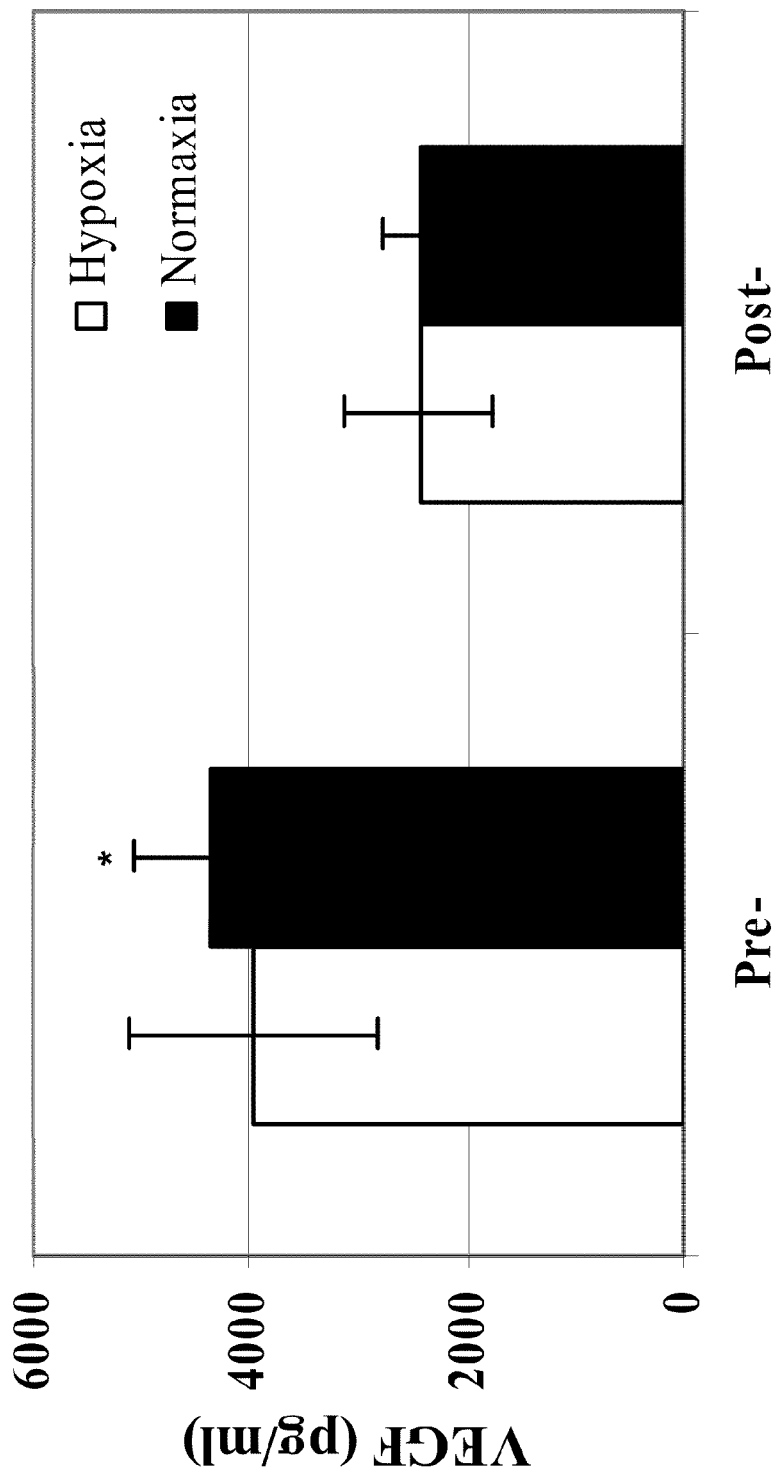
FIG. 6 shows differences in levels of VEGF between primary NHEK cells grown under the pre- or post-menopausal conditions and after exposure to 1% $O_2$ for 6 h or normoxia only. * indicates a significant difference from cells grown under post-menopausal conditions.
Figure 7:
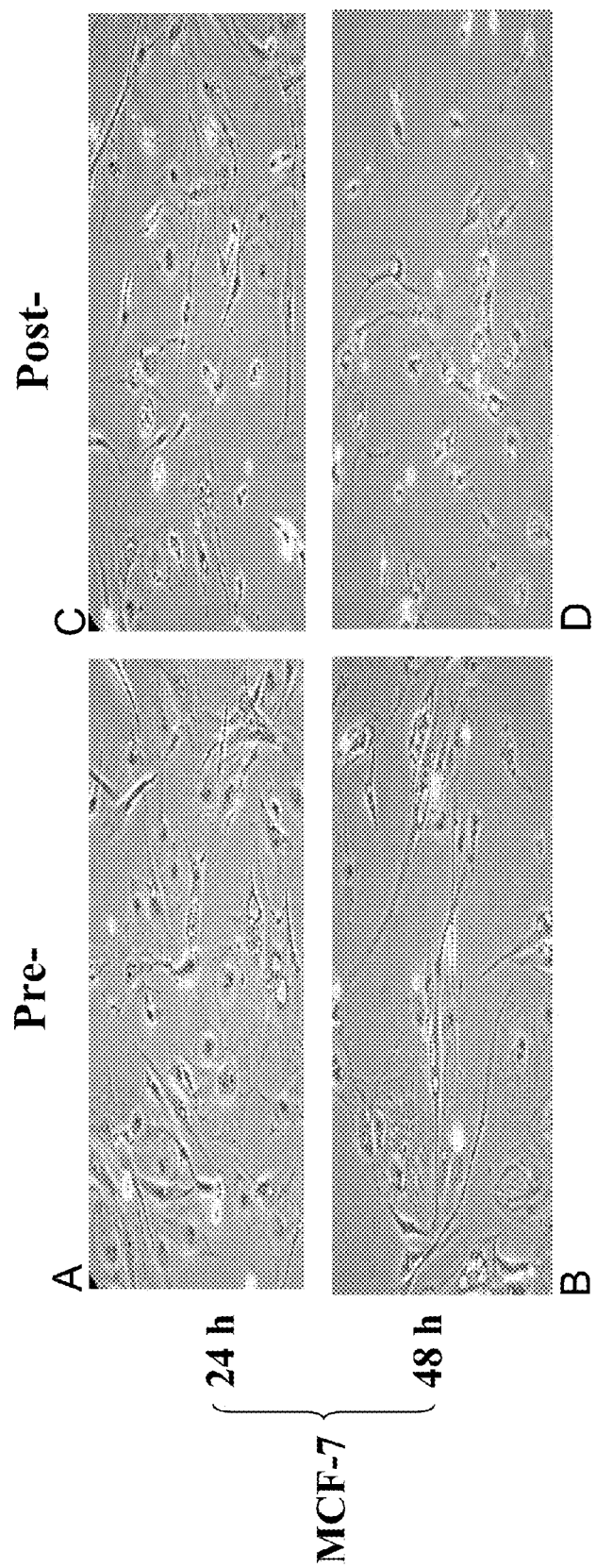
FIGS. 7A-D show differences in morphology between BCE cells incubated with culture media collected from MCF-7 cells grown under the pre-(FIGS. 7A, B) or post-menopausal (FIGS. 7C, D) conditions for 24 h or 48 h, respectively.
Figure 8:
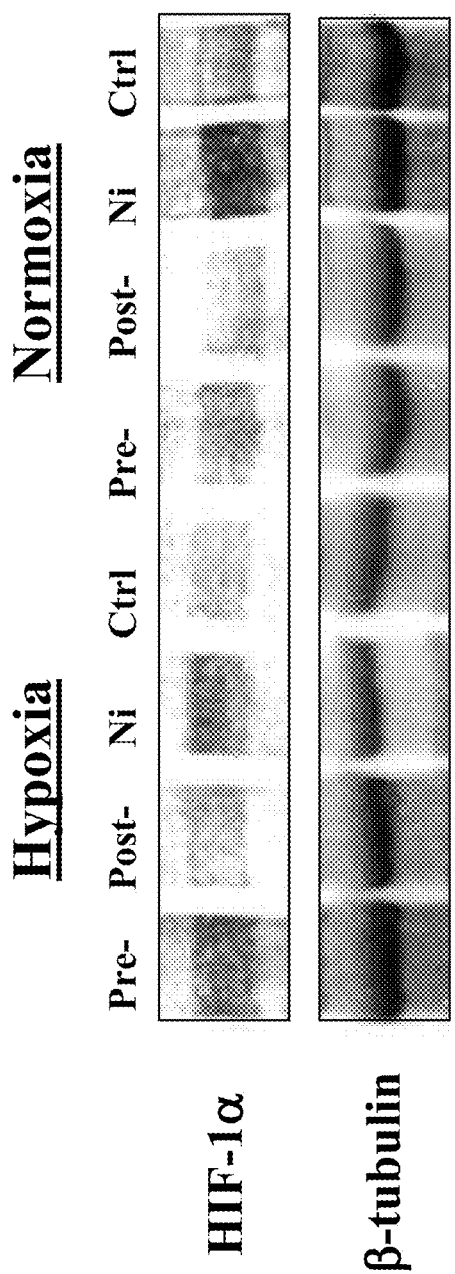
FIG. 8 shows differences in HIF-1α stability between MCF-7 cells grown under the pre- or post-menopausal conditions and exposed to 1% $O_2$ or normoxia for 6 h. Ni was used as a positive control for HIF-1α induction and β-tubulin shows an equal loading of proteins.

The choice of vascular endothelial growth factor (VEGF) as a target gene for this study is based on the facts that VEGF plays a role in bone formation and has been associated with a poor prognosis of breast cancer in young patients (Gasparini G., "Prognostic Value of Vascular Endothelial Growth Factor in Breast Cancer," *Oncologist* (5 Suppl.) 1:37-44 (2000), which is hereby incorporated by reference in its entirety). The MCF-7 cells grown in conditions mimicking the pre-menopausal state, with high E2 and low Fe, produced high levels of VEGF following a 6 h exposure to hypoxic conditions. The increased VEGF levels persisted when culture conditions were shifted to normoxic conditions (FIG. 5). These same cells, grown in conditions mimicking the post-menopausal state, with low E2 and high Fe, yielded low levels of VEGF and were less responsive to hypoxic treatment. In the primary NHEK cell cultures, similar trends in VEGF formation were observed when pre- and post-menopausal conditions were compared (FIG. 6). It appears that hypoxia has no effect on VEGF in NHEK cells. When bovine capillary endothelial (BCE) cells were incubated with culture media collected from MCF-7 and grown in either pre- or post-menopausal conditions, this media, which contains high levels of E2 and low Fe levels, promoted the elongation of BCE cells, i.e. promoted angiogenesis. In contrast, BCE cells treated with low E2 and high Fe media appeared atrophied (FIG. 7). Hypoxia-inducible factor-1 alpha (HIF-1α) is a major modulating factor in VEGF expression, and the differences in VEGF levels between the two experiments were likely due to differences in HIF-1α stabilization (FIG. 8).

Figure 9:
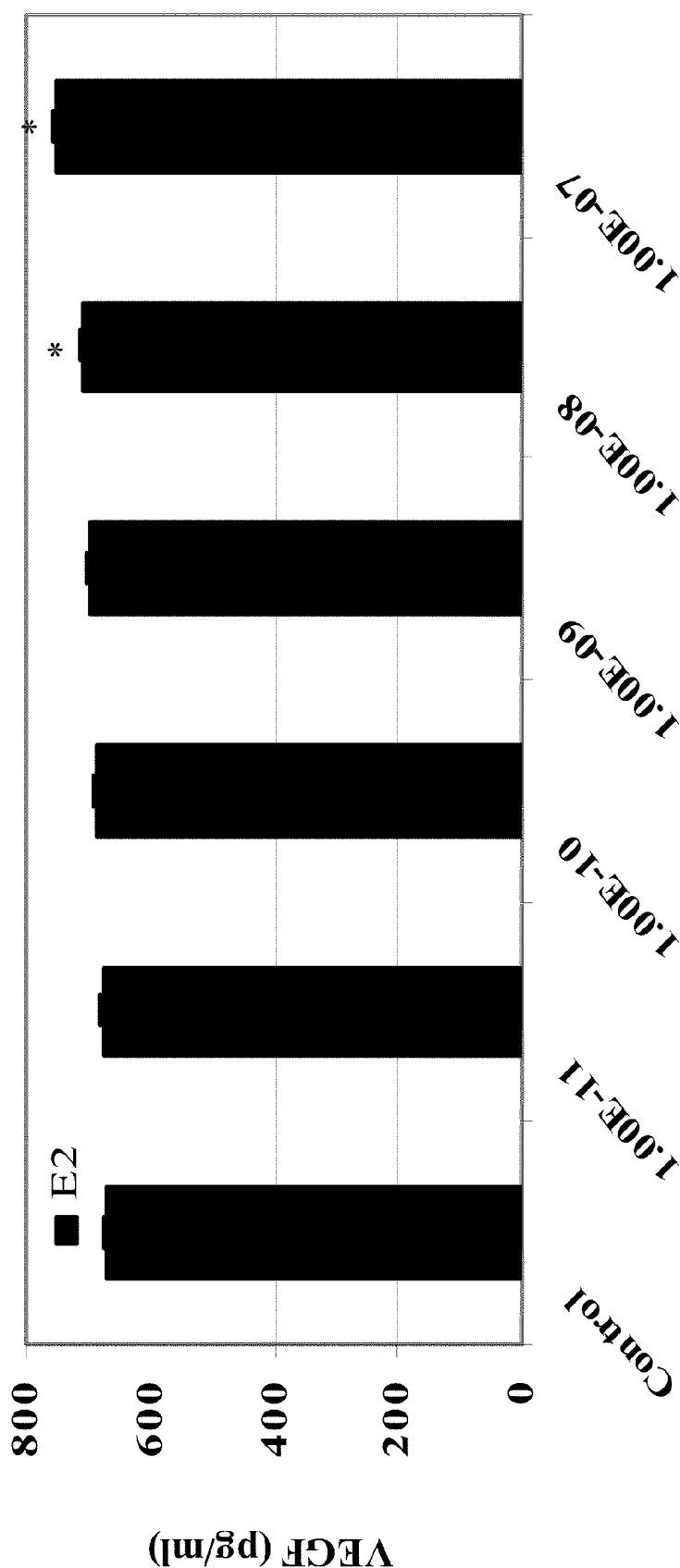
FIG. 9 shows minor stimulating effects of E2 at various concentrations for a 24-hr treatment on VEGF formation in MCF-7 cells. * indicates a significant difference from untreated control cells.
Figure 10:
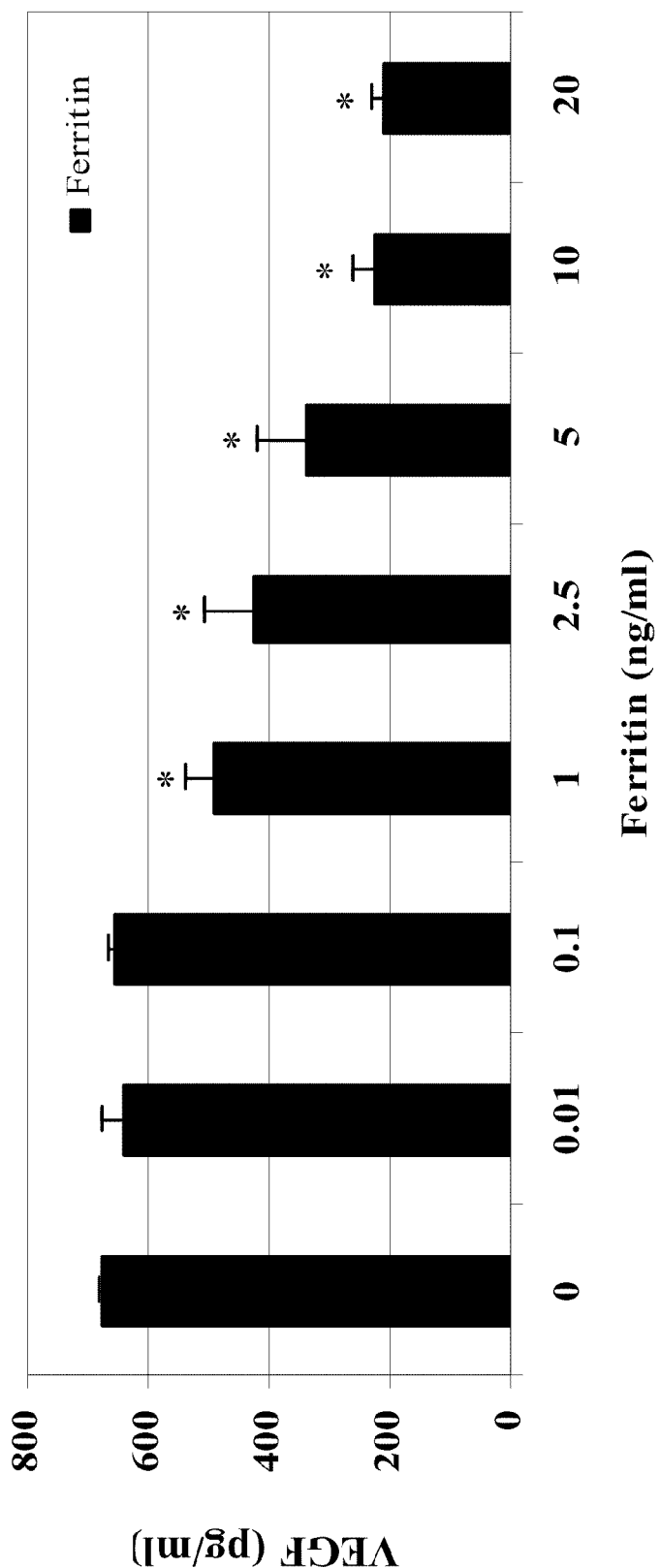
FIG. 10 shows inhibitory effects of ferritin at various concentrations for a 24-hr treatment on VEGF formation in MCF-7 cells. * indicates a significant difference from untreated control cells.
Figure 11:
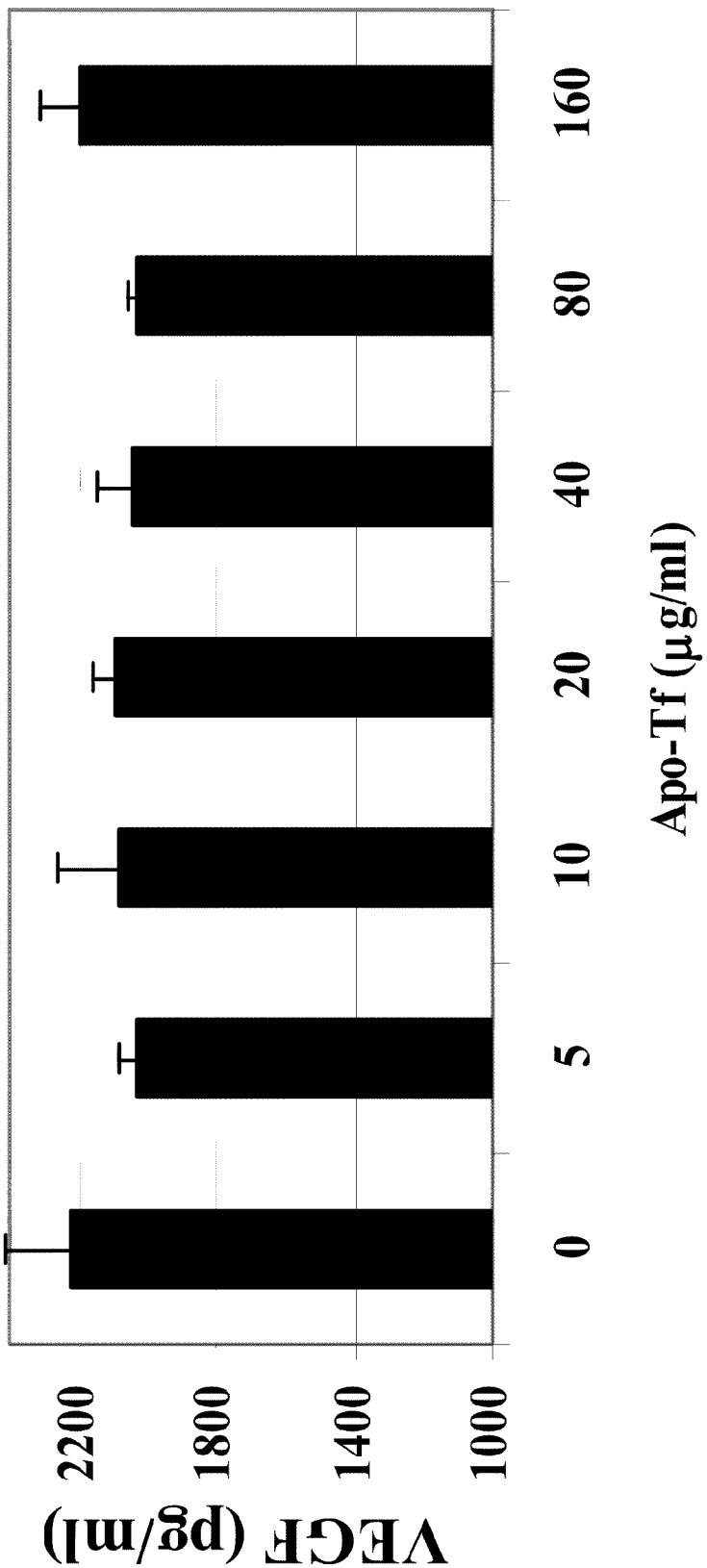
FIG. 11 shows no effects of apo-transferrin (Apo-Tf, without iron in it) at various concentrations for a 24-hr treatment on VEGF formation in MCF-7 cells.
Figure 12:
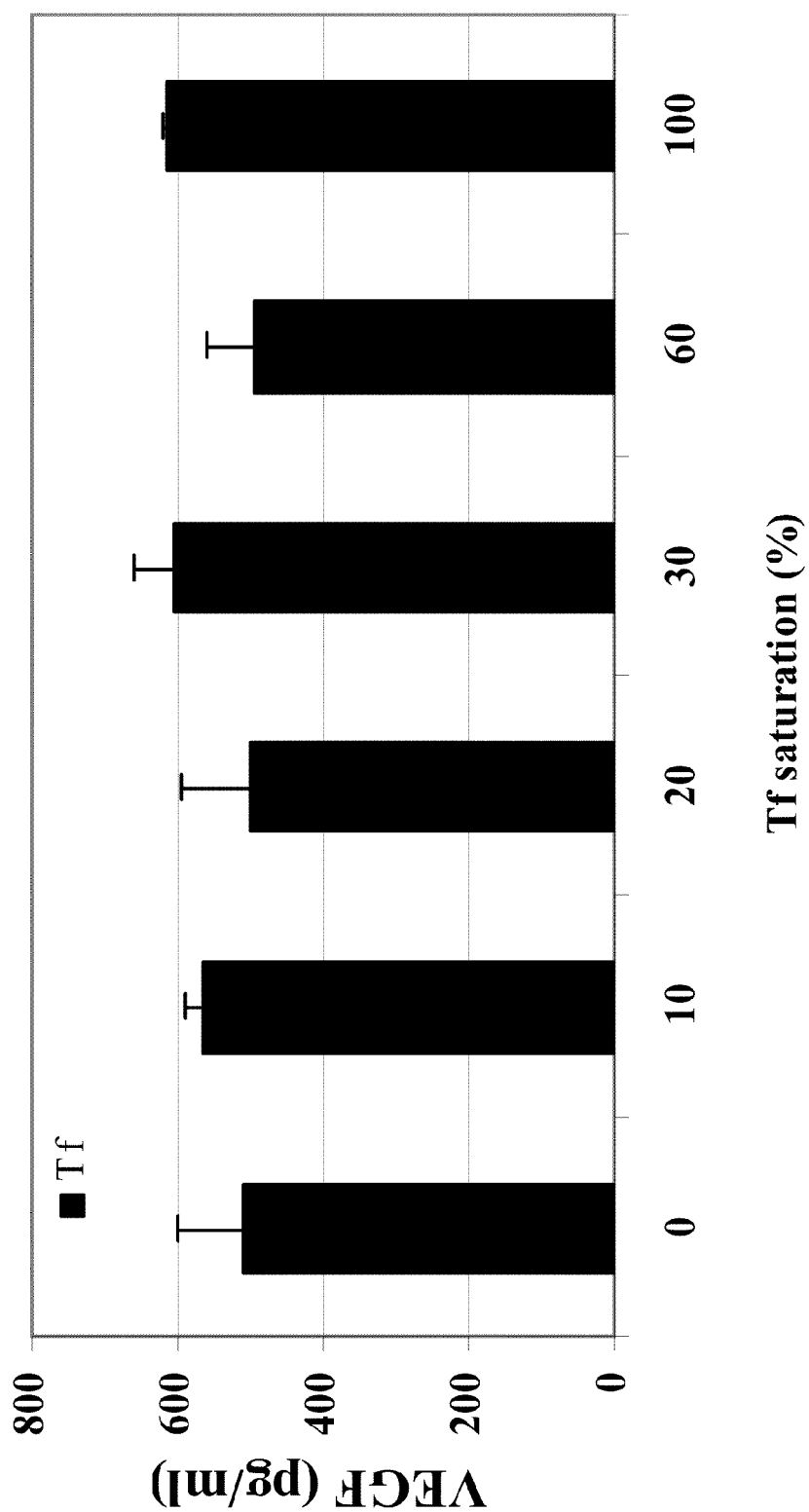
FIG. 12 shows no effects of transferrin at the same concentration (5 μg/ml) but different iron saturation for a 24-hr treatment on VEGF formation in MCF-7 cells.

E2, transferrin, and ferritin were analyzed separately in MCF-7 cell cultures to determine their relative contribution to alterations in VEGF levels. FIG. 9 demonstrates some increase in VEGF formation with the addition of E2. Importantly, FIG. 10 shows that the addition of ferritin significantly decreases VEGF levels in a dose-dependent manner. FIGS. 11 and 12 show that apo-transferrin at various concentrations or transferrin at various iron saturation levels had no effect on VEGF formation.

Example 3

Study on Effects of an Increase in Iron Levels in Cell Cultures

Figure 13:
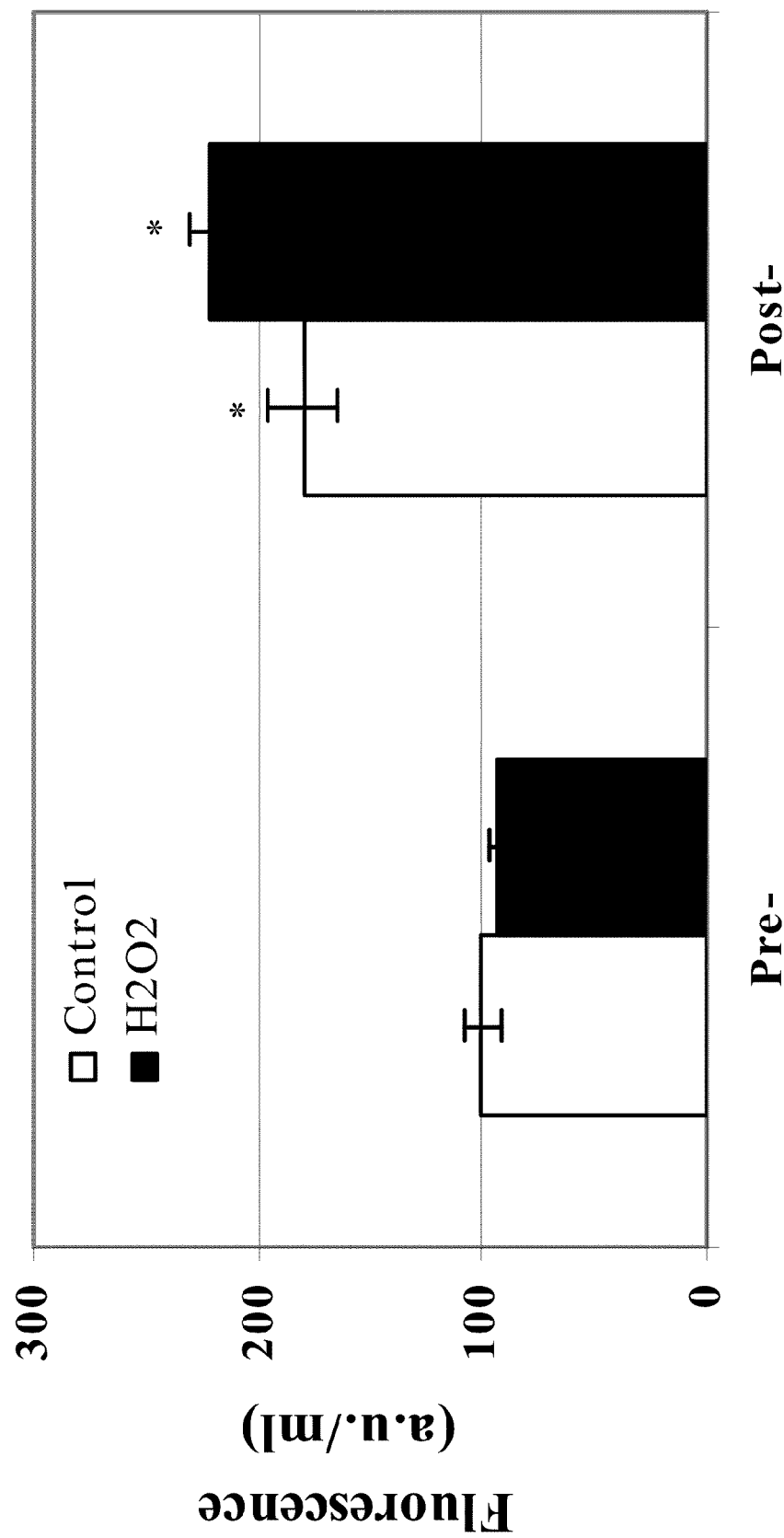
FIG. 13 shows differences in levels of lipid peroxidation between MCF-7 cells grown under the pre- or post-menopausal conditions and after exposure to $H_2O_2$ (10 μM) for 4 hr. * indicates a significant difference from cells grown under pre-menopausal conditions. a.u. are arbitrary units.
Figure 14:
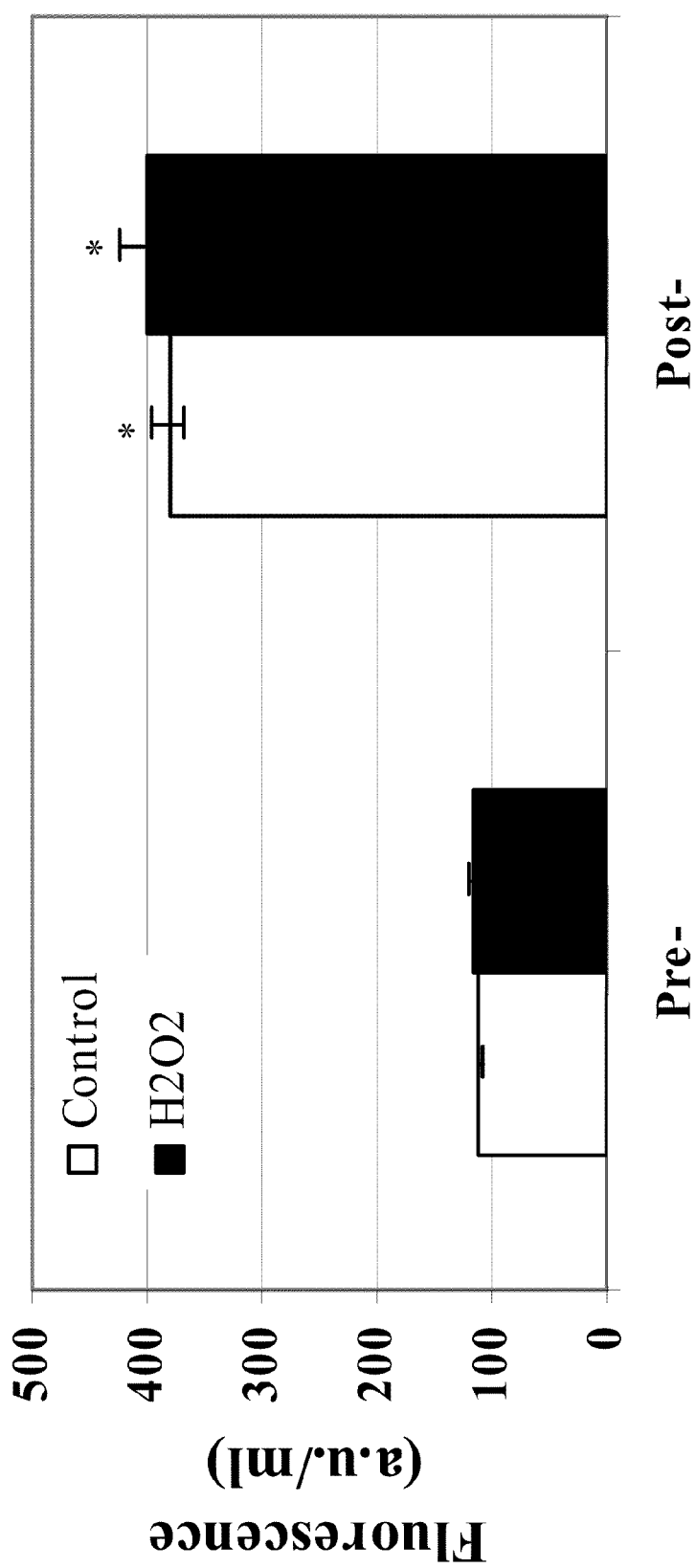
FIG. 14 shows differences in levels of lipid peroxidation between primary NHEK cells grown under the pre- or post-menopausal conditions and after exposure to $H_2O_2$ (10 μM) for 4 hr. * indicates a significant difference from cells grown under pre-menopausal conditions. a.u. are arbitrary units.
Figure 15:
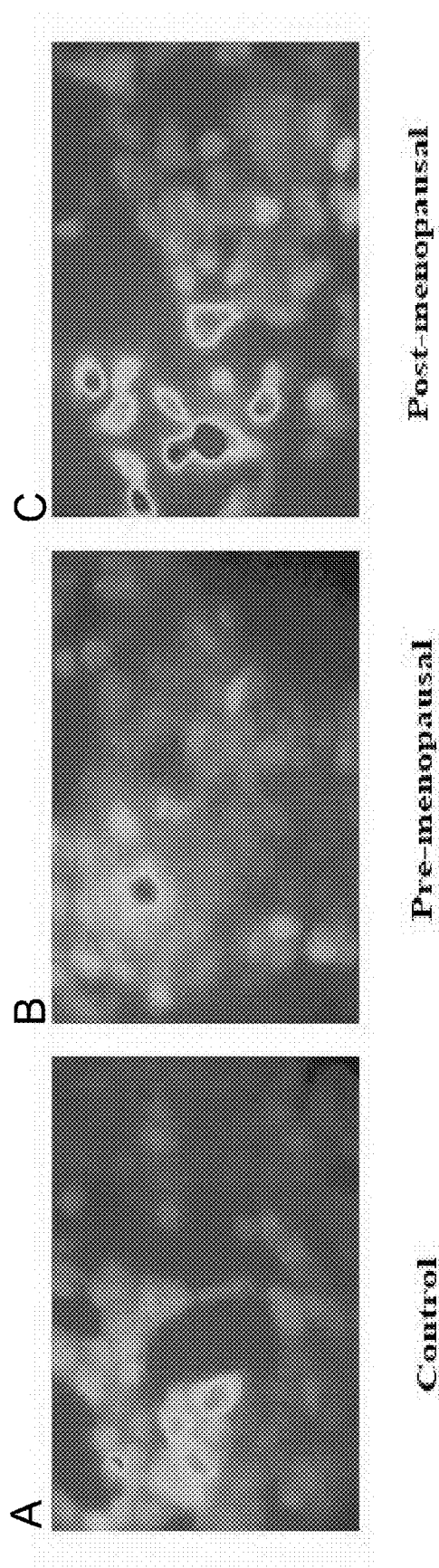
FIGS. 15A-C show differences in fluorescence intensities among MCF-7 cells grown under the control (FIG. 15A), pre- (FIG. 15B), and post-menopausal (FIG. 15C) conditions after cells were incubated with dichlorofluorescin diacetate for 0.5. h.
Figure 16:
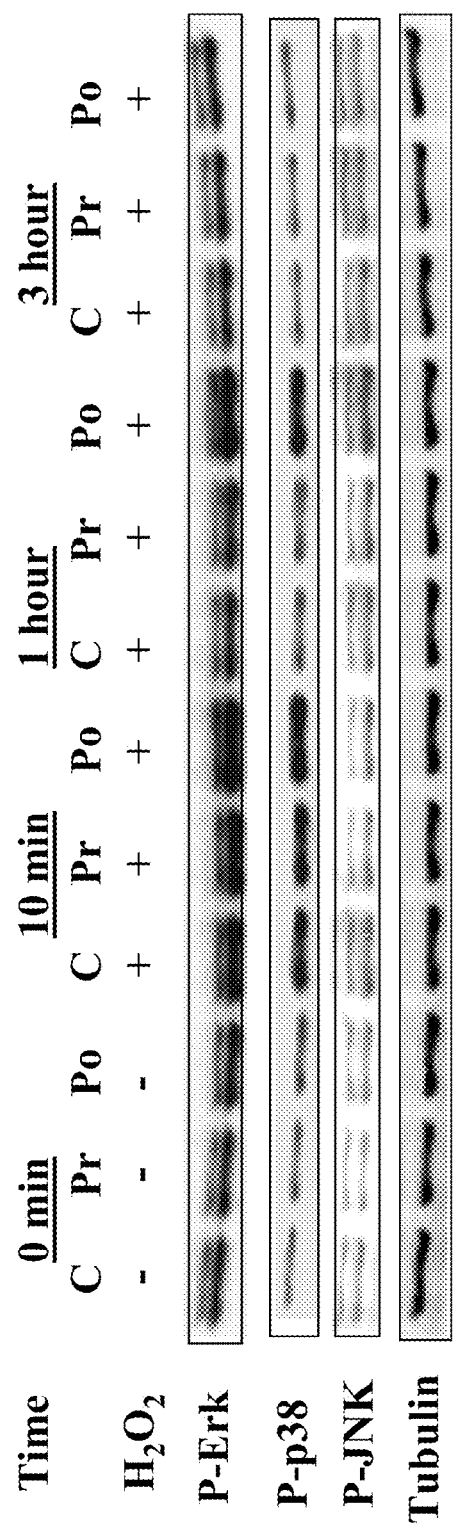
FIG. 16 shows differences in durability of ERK, p38, and JNK phosphorylation among MCF-7 cells grown under control, pre-, and post-menopausal conditions and after cells were exposed to 10 μM $H_2O_2$ for various times.

It is well known that iron catalyzes Fenton reactions that lead to the formation of reactive oxygen species. To investigate whether increased iron levels after menopause contribute to development of breast cancer, skin aging, and osteoporosis, various cells were tested in in vitro systems. MCF-7 and NHEK cells grown in post-menopausal conditions of low E2 and high Fe, were more sensitive to oxidative damage (measured by lipid peroxidation) as compared to the same cells grown in pre-menopausal conditions of high E2 and low Fe (FIGS. 13 and 14). Initial starting levels of lipid peroxidation were high in MCF-7 and NHEK cells grown in conditions imitating post-menopause. Additionally, MCF-7 and NHEK cells grown in pre- but not post-menopausal conditions, were protected from $H_2O_2$—induced lipid peroxidation (10 μM $H_2O_2$ for 4 h). Addition of the fluorescent oxidant probe, 2',7'dichlorodihydrofluorescin diacetate, to MCF-7 cells grown under post-menopausal conditions resulted in an increase in oxidative stress as illustrated by the yellow-pink color (FIG. 15). Furthermore, phosphorylation of the three major mitogen-activated protein kinases (MAPK) pathways, Extracellular receptor kinase (ERKs), p38, and c-Jun N terminal kinase (JNK), in cells grown under post-menopausal conditions, was sustained longer in comparison with the same cells grown under control or pre-menopausal conditions when cells were challenged with $H_2O_2$ (FIG. 16).

Example 4

Study on Effects of Iron Levels on Bone Formation and Bone Resorption

Figure 17:
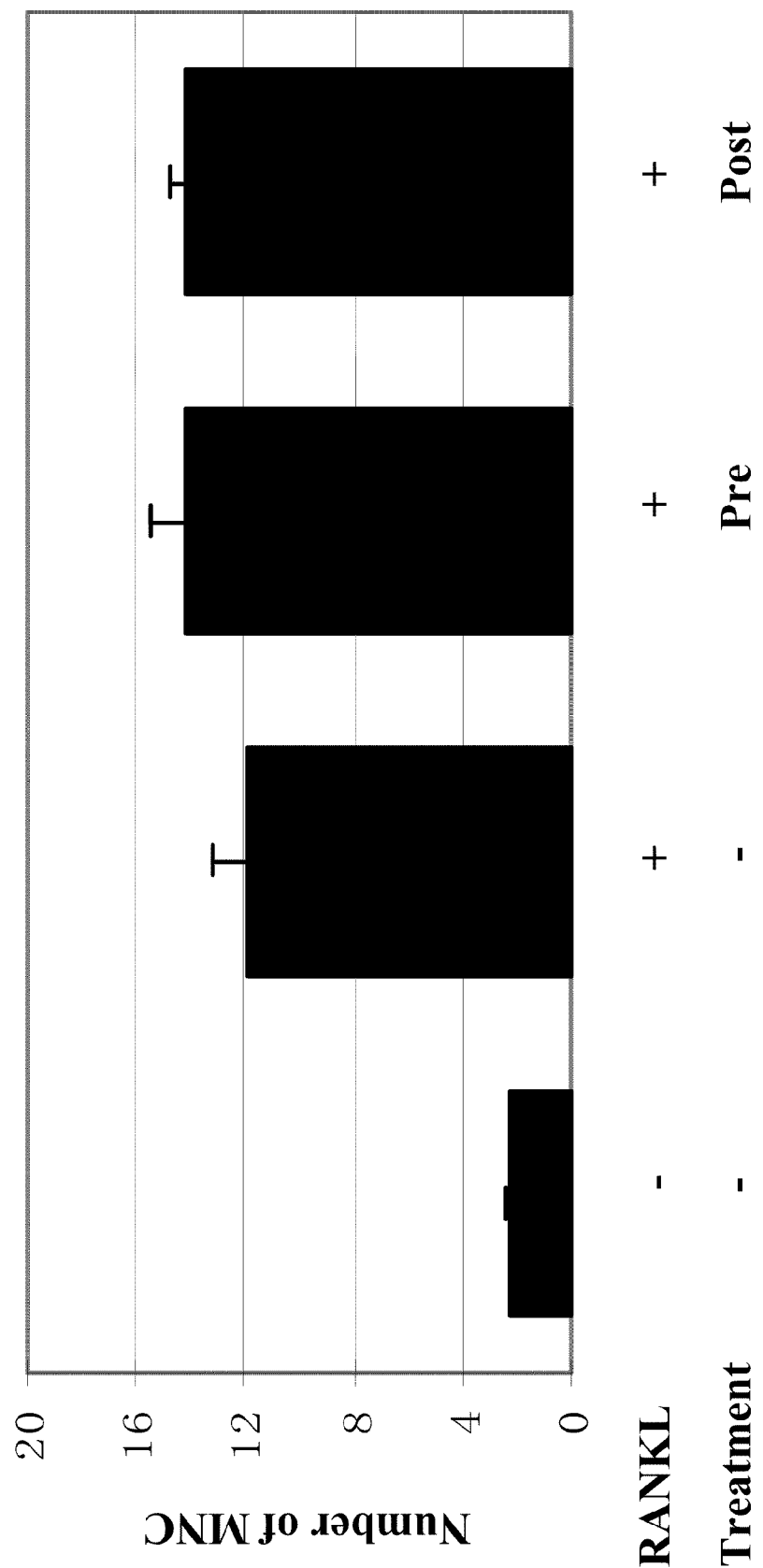
FIG. 17 shows no differences in differentiation of mouse osteoclast Raw 267.4 cells grown under the control, pre-, and post-menopausal conditions in the presence of receptor activator of nuclear factor kappa B ligand (RANKL) at 50 ng/ml for 5 days. The numbers of TRAP-positive MNC (more than three nuclei) cells per 500 cells were shown.
Figure 18:
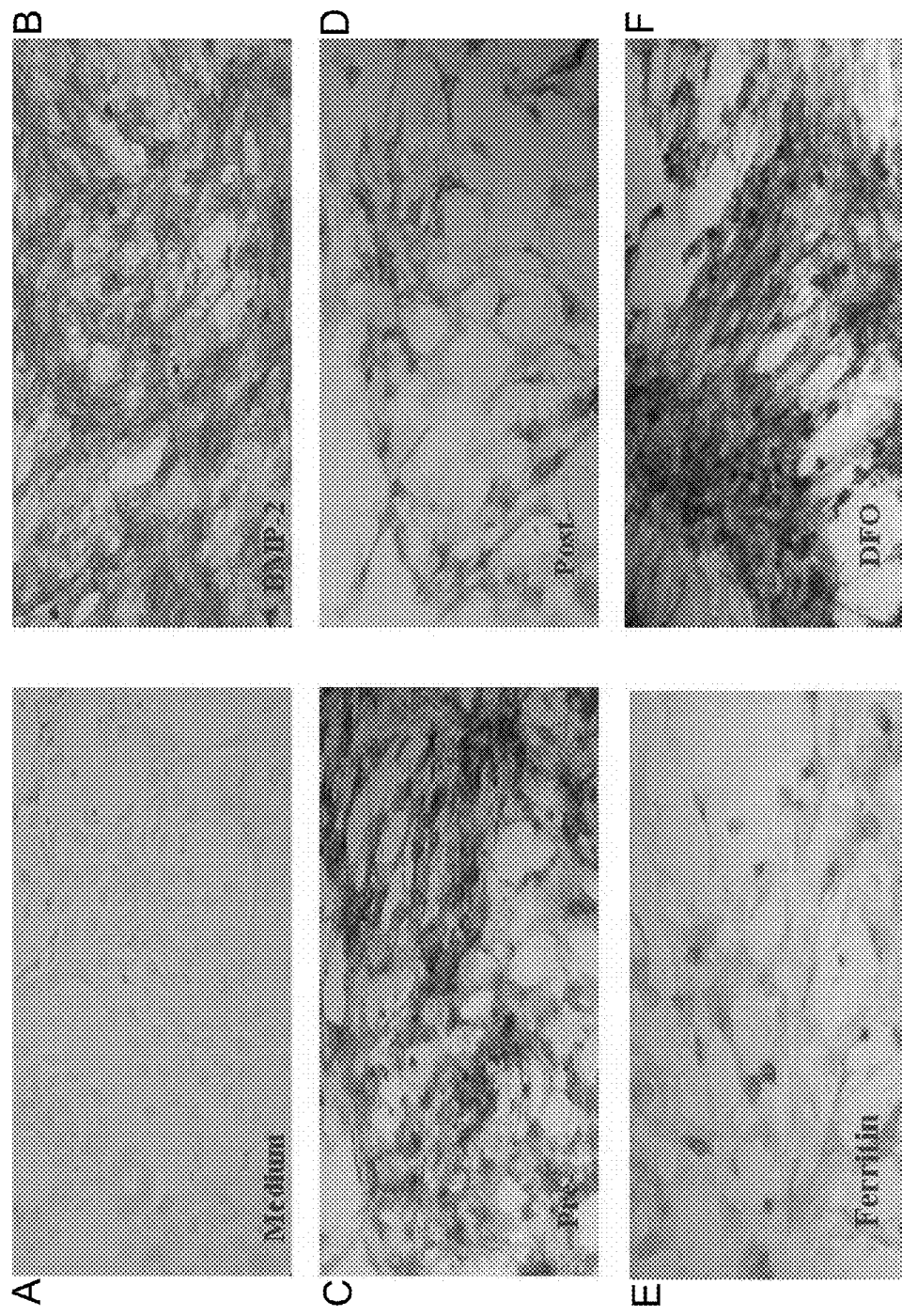
FIGS. 18A-F show differences in alkaline phosphates (ALP) activities in mouse osteoblast C2C12 cells grown in medium only (FIG. 18A), with bone morphorgenetic protein-2 (BMP-2) (FIG. 18B), under the pre-menopausal (FIG. 18C), post-menopausal (FIG. 18D), with ferritin (FIG. 18E), and with deferoxamine (DFO) (FIG. 18F). DFO, an iron chelator, (10 μM) or ferritin alone (20 ng/mL) was used in the presence of BMP-2 at 50 ng/ml.
Figure 19:
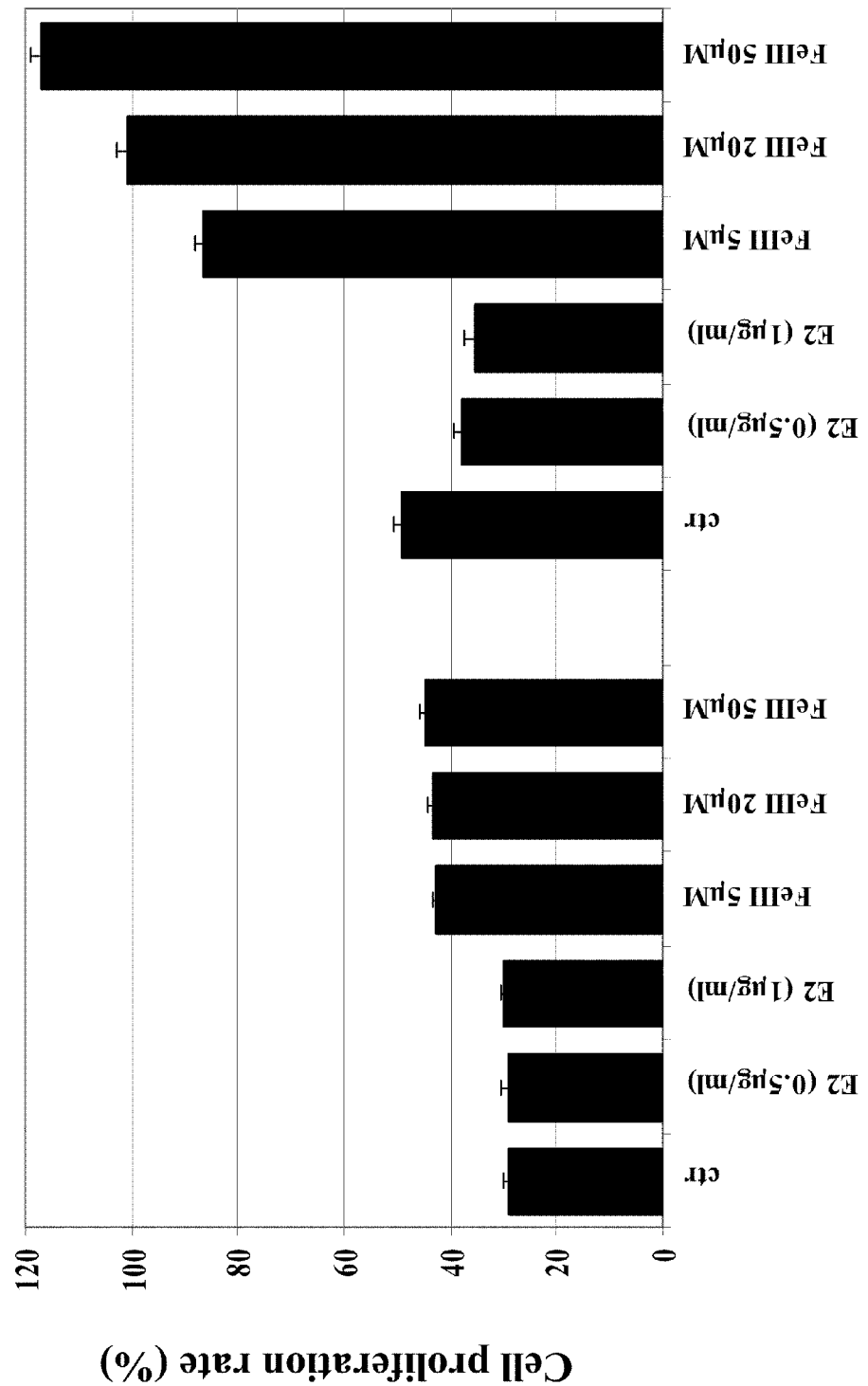
FIG. 19 shows stimulating effects of iron but not E2 on C2C12 cell proliferation.
Figure 20:
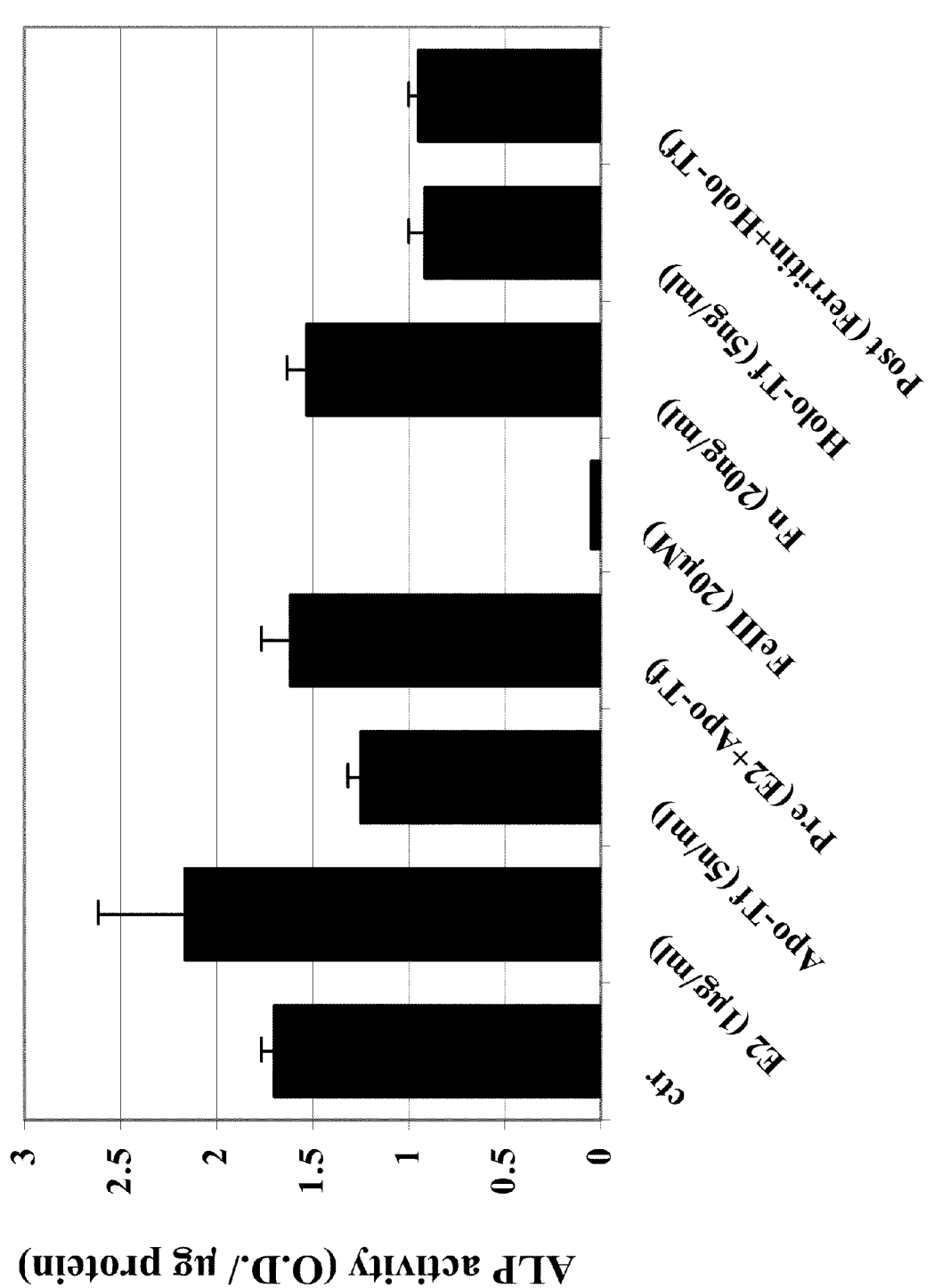
FIG. 20 shows inhibitory effects of iron on C2C12 cell differentiation as marked by the ALP activity.

To investigate whether increased iron levels affect the balance between bone formation and bone resorption, mouse osteoblasts C2C12 and osteoclasts Raw 264.7 cells were cultured in the two distinct media. FIG. 17 shows that, in the presence of RANKL, pre- and post-menopausal condition had no significant effects on osteoclast differentiation as measured by the number of tartrate-resistant acid phosphatase (TRAP)-positive and multinucleated cells (MNC), a marker of osteoclast differentiation. However, osteoblast C1C12 cells grown under post-menopausal conditions demonstrate that, in the presence of BMP-2, significant inhibition was observed on the formation of alkaline phosphatase, a biomarker for bone formation, as compared to the same cells grown under pre-menopausal conditions (FIG. 18). In other experiments, the iron chelator deferoxamine (DFO), promoted alkaline phosphatase production, whereas ferritin diminished it. These results indicate that increased iron inhibits bone formation. Increased iron did not, however, significantly effect osteoclasts Raw 264.7 cell differentiation as determined by the TRAP-positive MNC cells and shown in FIG. 17. To further search how increased iron affect osteoblasts, C2C12 cells were grown in the presence of E2 or iron over a period of 3 and 5 days. Cell proliferation was then measured. FIG. 19 shows that E2 did not increase cell proliferation over time, but significant proliferation was observed in the presence of iron. Interestingly, FIG. 20 shows that osteoblast differentiation, as measured by alkaline phosphates activity, were strongly inhibited by the presence of inorganic iron, and to a lesser extent, by holo-transferrin, or post-menopausal conditions, but slightly stimulated by E2. These results indicate that, in contrast to E2, which is known to have a mode of action by increasing bone resorption, increased iron mainly slows down bone formation by increasing osteoblast proliferation and decreasing its differentiation to mature osteoblasts.

Example 5

Study of the Effects of High Iron Diet on Mice

Figure 21:
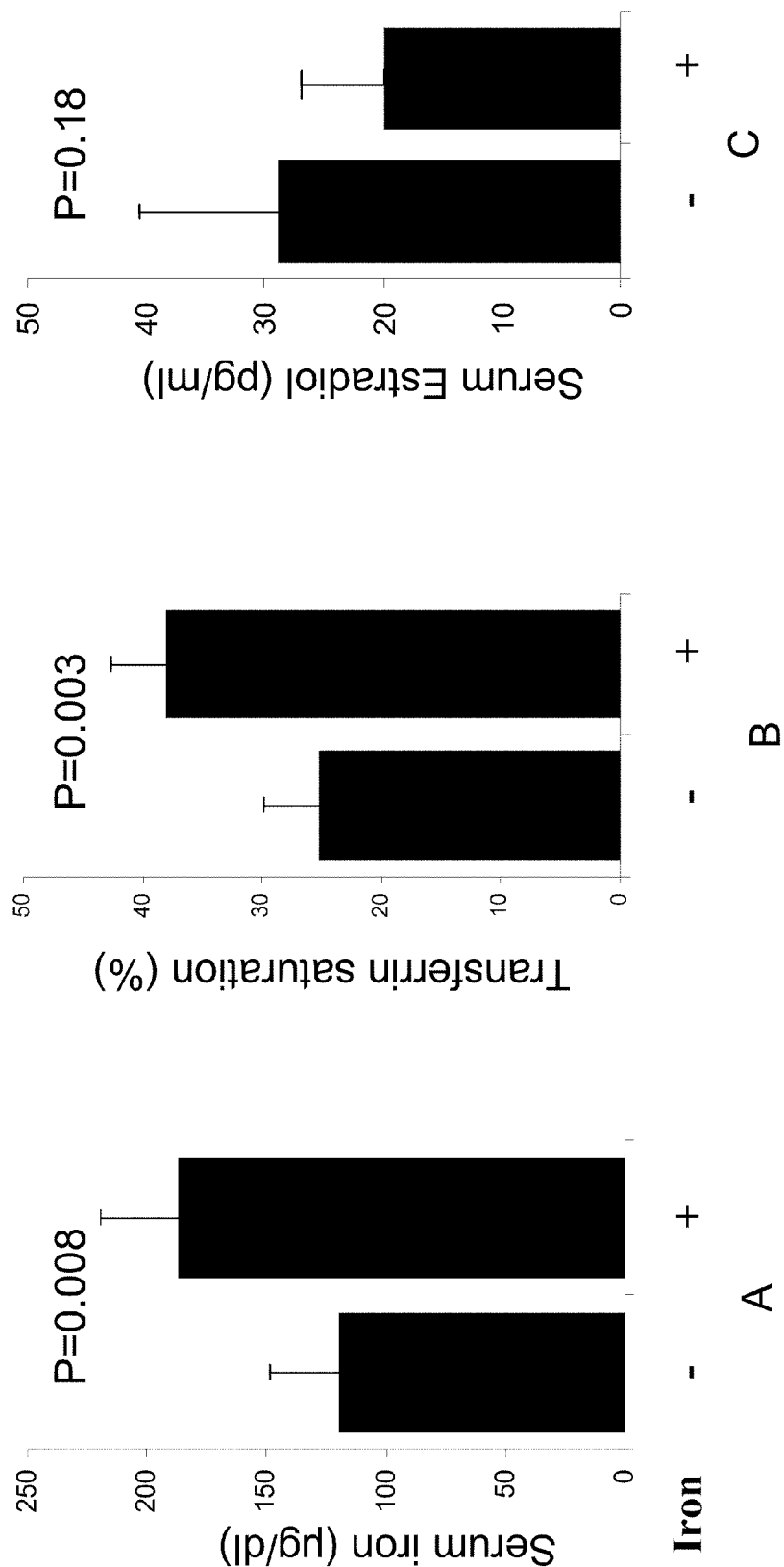
FIGS. 21A-C show levels of serum iron (FIG. 21A), transferrin saturation (FIG. 21B), and E2 (FIG. 21C) in mice fed normal or iron-enriched diets (n=5 per group).
Figure 22:
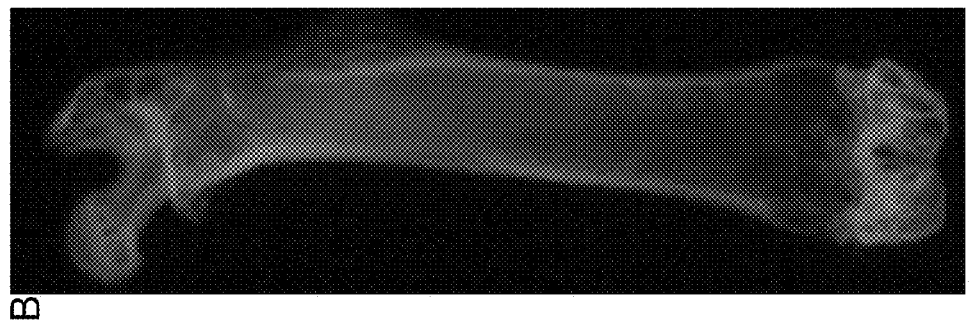
FIGS. 22A-B show a representative soft X-ray image of the bones of mice fed normal (FIG. 22A) or iron-enriched diets (FIG. 22B).
Figure 22:
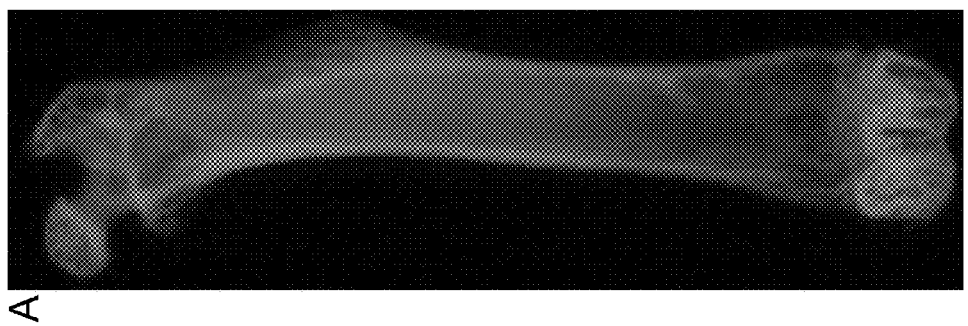
Figure 23:
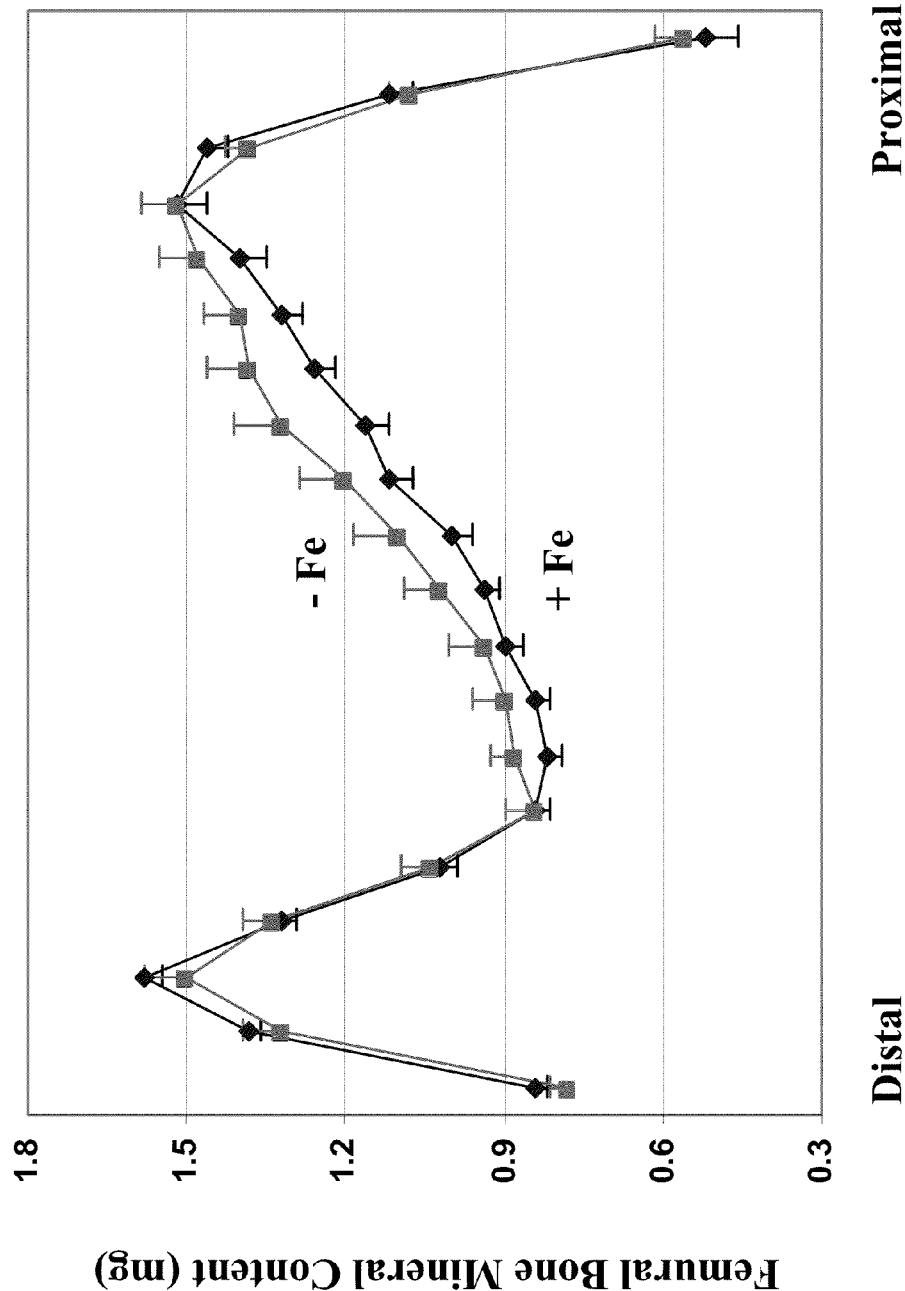
FIG. 23 shows differences in average levels of femur bone mineral content between mice fed normal or iron-enriched diets (n=5 per group).
Figure 24:
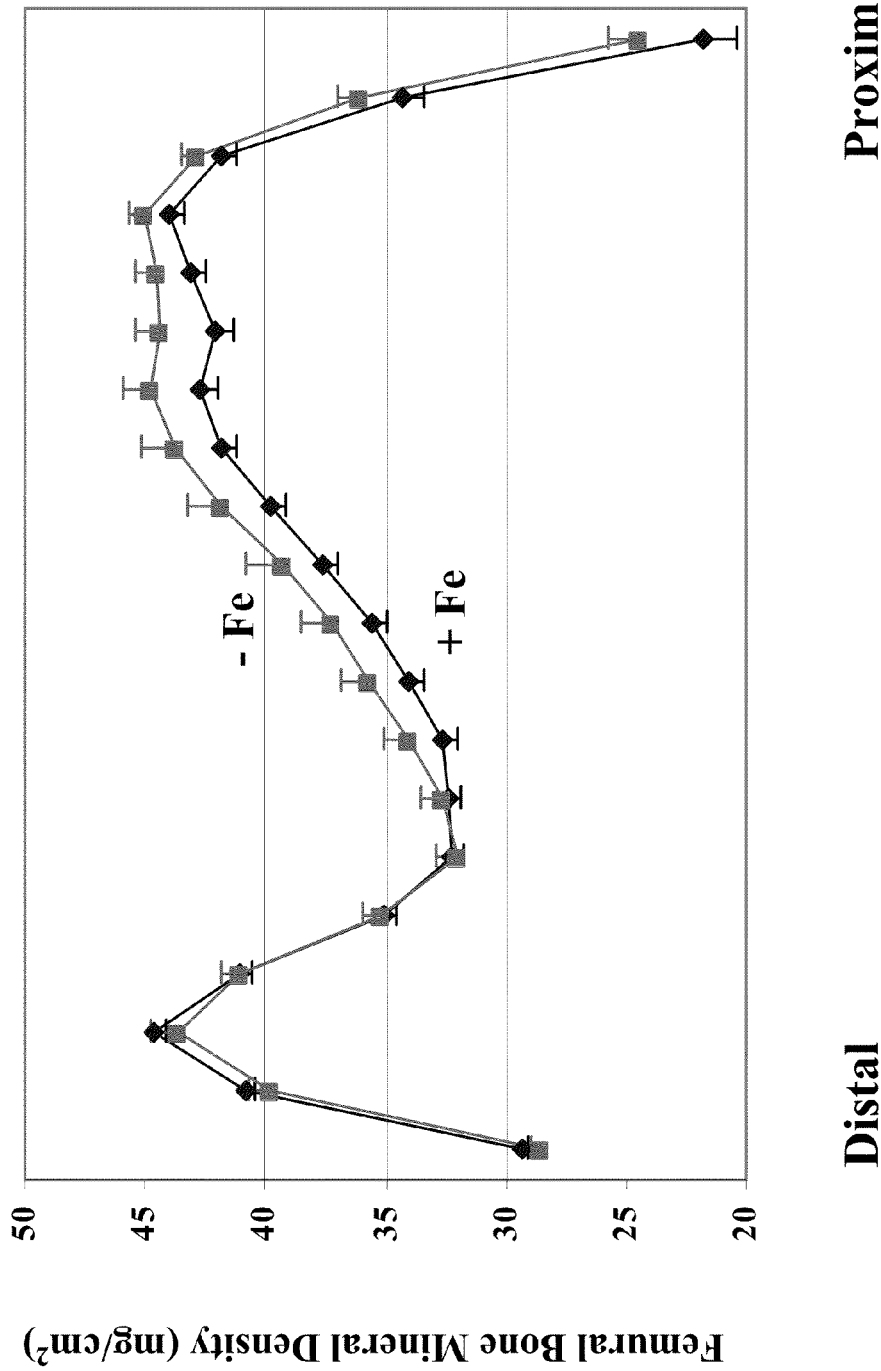
FIG. 24 shows differences in average levels of femur BMD between mice fed normal or iron-enriched diets (n=5 per group).

To further provide in vivo evidence that increased iron contributes to osteoporosis development, mice were fed a high iron diet. Control mice were fed a normal diet. After 16 months over the mouse life span of 24 months, mice were sacrificed. Serum samples were collected for iron and E2 levels and bone samples were collected for BMD analyses. FIG. 21 shows that mice fed iron-enriched diet had significantly higher levels of serum iron and transferrin saturation than mice fed normal diet. E2 levels remain low after 16 months and, thus, simulate menopause. Interestingly, E2 levels were comparable between the two groups of mice fed normal or iron-enriched diets. FIG. 22 shows the image of the soft X-ray of the femur of mice fed normal or iron-enriched diets, indicating a lower BMD in mice fed iron. FIG. 23 demonstrates that bone mineral contents were significantly lower in the group of 5 mice fed iron as compared to those fed normal diet. FIG. 24 shows that the BMD is also lower in mice fed iron than those fed normal diet.

Taken together, it could be concluded that increased iron contributes to post-menopausal osteoporosis in a mode of action that is different from estrogen. Increased iron is a risk factor that is independent of estrogen deficiency in menopausal symptoms and diseases.

Example 6

Study of the Effects of Hepcidin on Mice

Human body has many ways to absorb, transfer, and store iron but has no effective ways to excrete it (Andrews N. C., "Disorders of Iron Metabolism," *N Engl J Med* 341:1986-95 (1999), which is hereby incorporated by reference in its entirety). Menstruation, which can get rid of iron in young premenopausal women, is not optional in older postmenopausal women. Therefore, hepcidin and deferoxamine (DFO), a FDA-approved iron chelator, were tested to see whether hepcidin or DFO can inhibit iron absorption and decrease body iron levels. After overnight fasting, mice were injected intra-peritoneally (i.p.), twice a week, with hepcidin at 1.5 mg/kg, DFO at 400 mg/kg, or saline (control) with 10 mice per group. After 8 weeks consecutive treatment, mice were sacrificed and blood were collected by heart puncture. Serum samples were used for measurements of serum iron and transferrin saturation.

Figure 25:
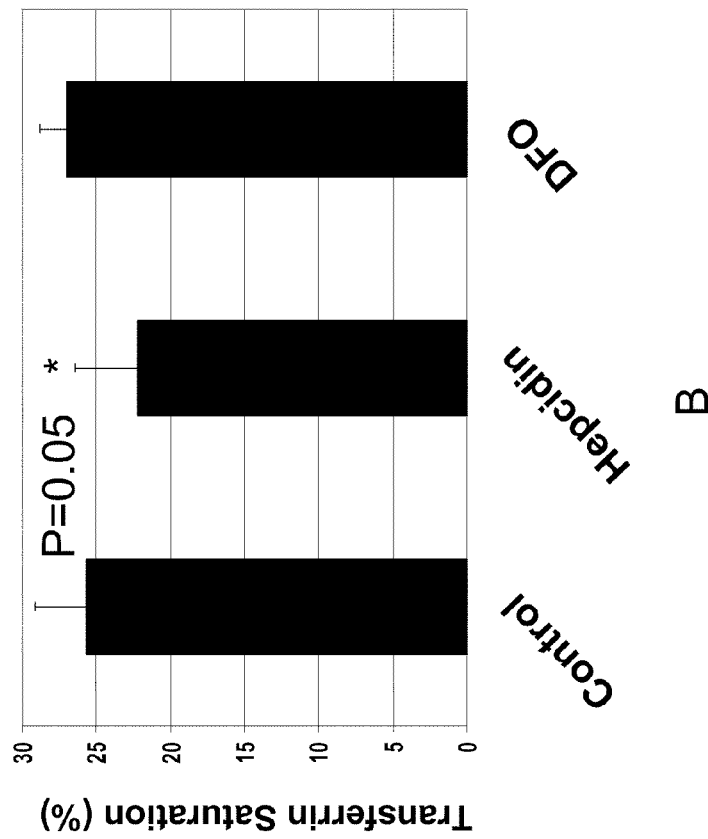
FIGS. 25A-B shows the shows levels of serum iron ((FIG. 25A) and transferrin saturation (FIG. 25B) in mice treated with hepcidin or deferoxamine (n=10 per group). After overnight fasting, mice were injected with hepcidin at 1.5 mg/kg or deferoxamine (DFO) at 400 mg/kg i.p. twice a week for 8 weeks. Control mice were injected with saline. Data were presented as mean±SD.
Figure 25:
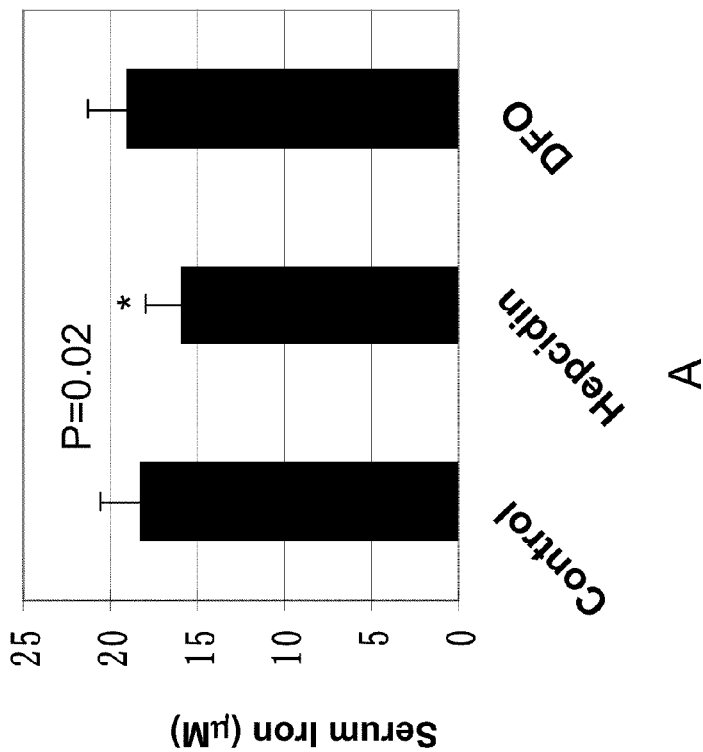

FIG. 25 shows that levels of serum iron and transferrin saturation in mice treated with hepcidin were significantly lower than in control mice or mice treated with DFO (n=10 per group). These results indicate that hepcidin is effective in inhibiting iron absorption and decreasing body iron levels.

Example 7

Study of the Effects of Iron on Estrogen Metabolism

Figure 26:
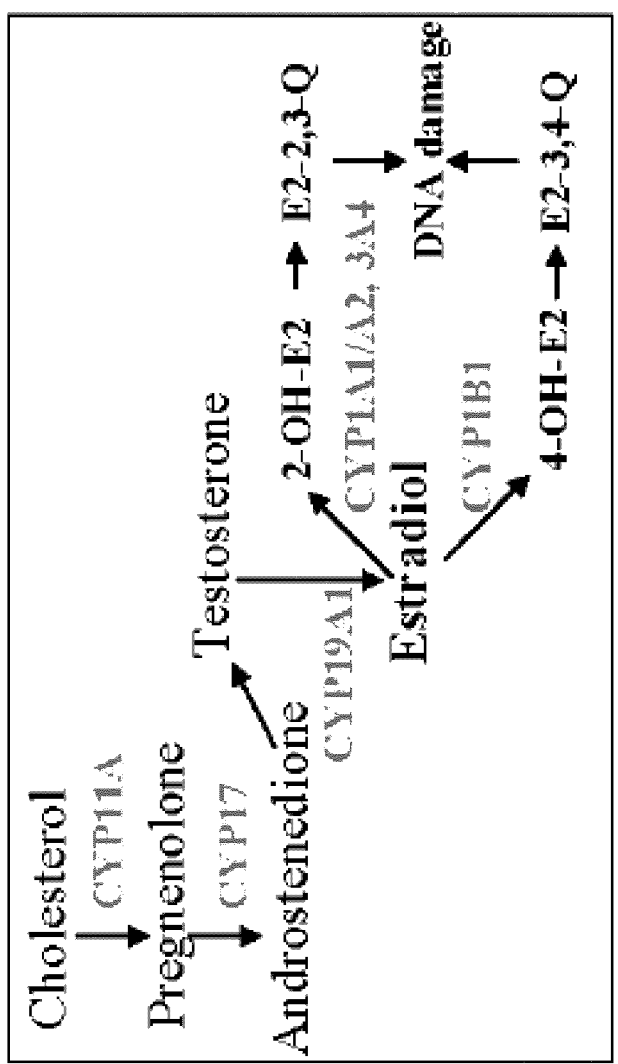
FIG. 26 shows Cytochrome P450-mediated metabolic pathways of E2.
Figure 27:
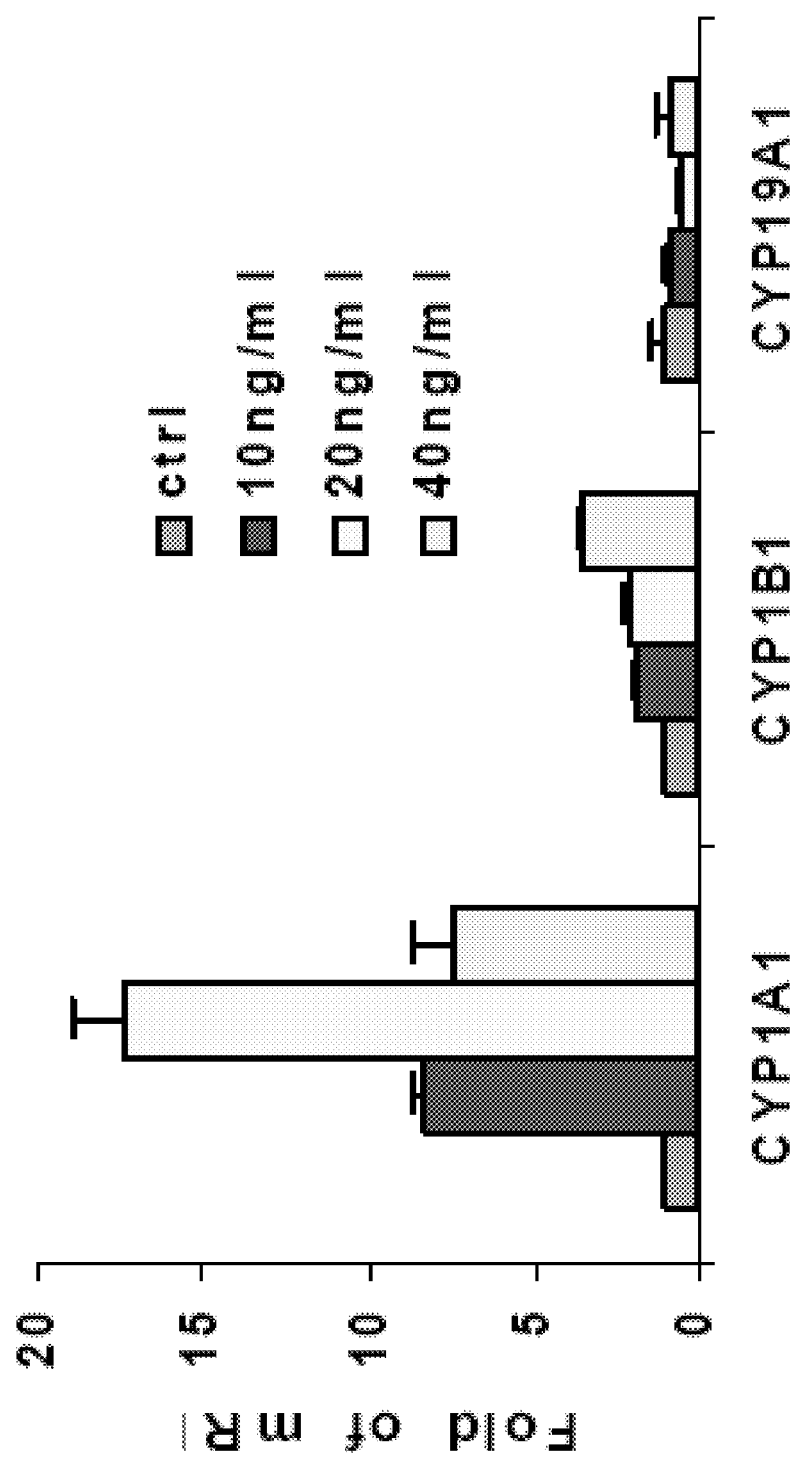
FIG. 27 shows the induction of CYP1A1 and CYP1B1, but not CYP19A1 by ferritin in MCF-12A cells.

It was also investigated whether increased iron as a result of menopause affects estrogen metabolisms. It is known that 95% of serum E2 in premenopausal women is derived from ovarian secretion and subsequently distributed through the bloodstream in an endocrine fashion. Almost all of the circulating E2 in postmenopausal women is from extragonadal conversion of C19 steroid precursors, principally weak adrenal androgens (FIG. 26). The conversion occurs locally in tissues such as adipose and bone marrow and E2 acts in a paracrine fashion. E2 is the most active form of estrogen providing the best benefits to the bone. Estrogens are eliminated from the body by metabolic conversion to estrogenically inactive and potentially carcinogenic metabolites. The first step in the metabolism of estrogens is the hydroxylation catalyzed by cytochrome P450 enzymes such as CYP1A1 and CYP1B1, leading to the formation of 2-hydroxyl-E2 (2-OH-E2) and 4-OH-E2, respectively (Tsuchiya et al., "Cytochrome P450-mediated Metabolism of Estrogens and Its Regulation In Humans," *Cancer Leu* 227, 115-24 (2005), which is hereby incorporated by reference in its entirety). The results have shown that ferritin, at a dose as little as 10 ng/ml, or 100 ng/ml of serum, significantly increased CYP1A1 and CYP1B1 but not CYP19A1 mRNA levels in immortalized nontumorigenic human breast epithelial cell MCF-12A cells (FIG. 27). These results suggest that increased iron 1) could accelerate estrogen metabolism and, thus, may decrease half life of E2 in a woman's body; 2) support the in vivo observation of much lower levels of E2 in mice fed iron than mice fed normal diet; 3) has no effects on androgen conversion to estrogen, which is catalyzed by CYP19A1.

Example 8

Study of the Effects of Iron in Mice with Surgically Induced Menopause

In order to closely mimic the high iron and low estrogen conditions in postmenopausal women, the present invention uses a previously established mouse model with innovative adaptation. Surgical induction of menopause by ovariectomy (OVX) in mice simulates one of the major postmenopausal aspects: estrogen deficiency. To adapt the need to incorporate iron into the OVX animal model, twenty mice per sham-operated and OVX mice were sub-divided into two groups and fed normal (175 ppm Fe, Dyets, Inc.) or iron-enriched diets (2100 ppm Fe) for 12 weeks. After sacrifice, the body weights of the mice were weighed and blood collected by heart puncture.

Figure 28:
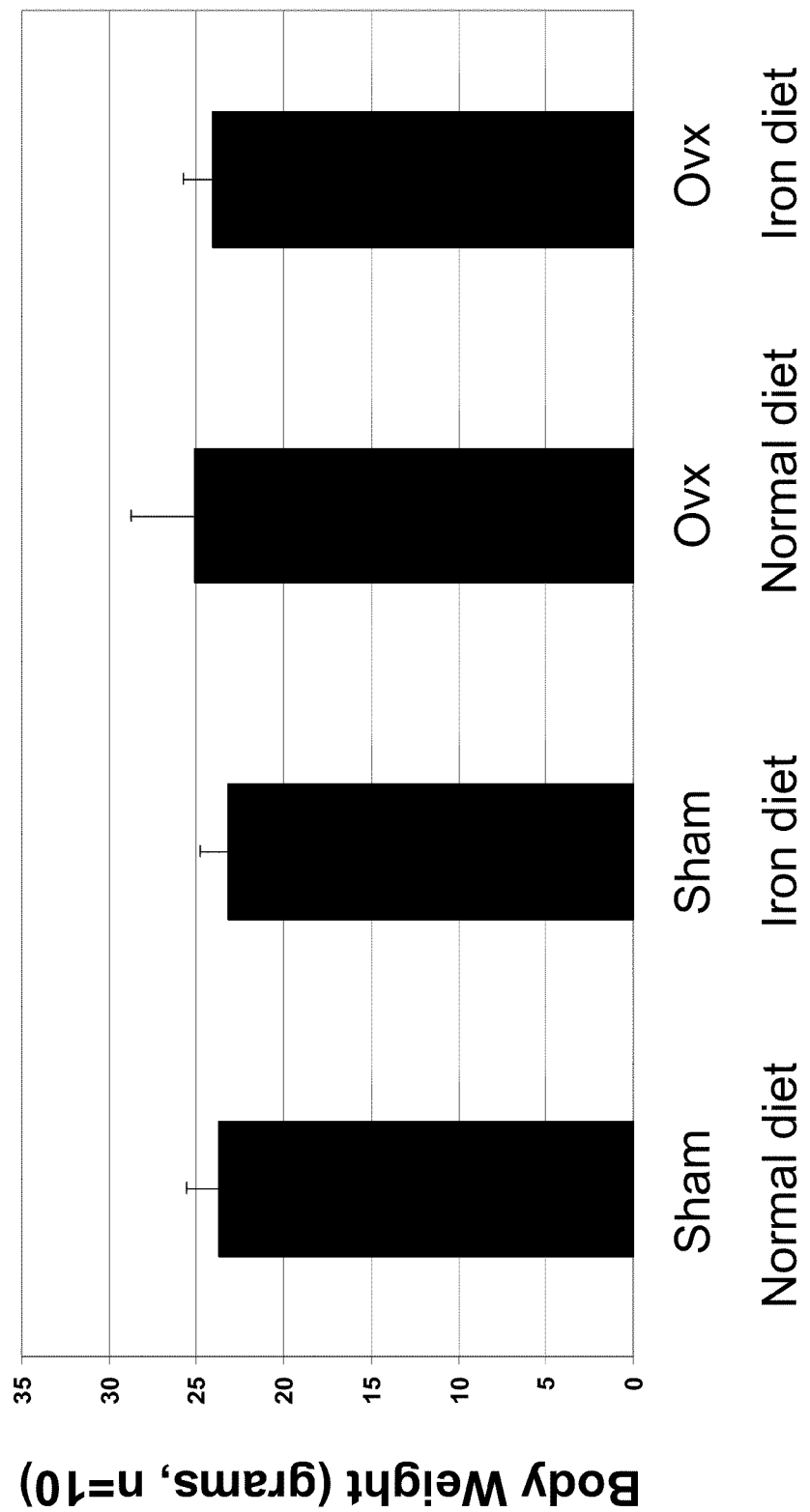
FIG. 28 shows no significant differences in body weights among groups fed iron-enriched or normal diets for 12 weeks, ovariectomized (Ovx) or sham-operated mice.
Figure 29:
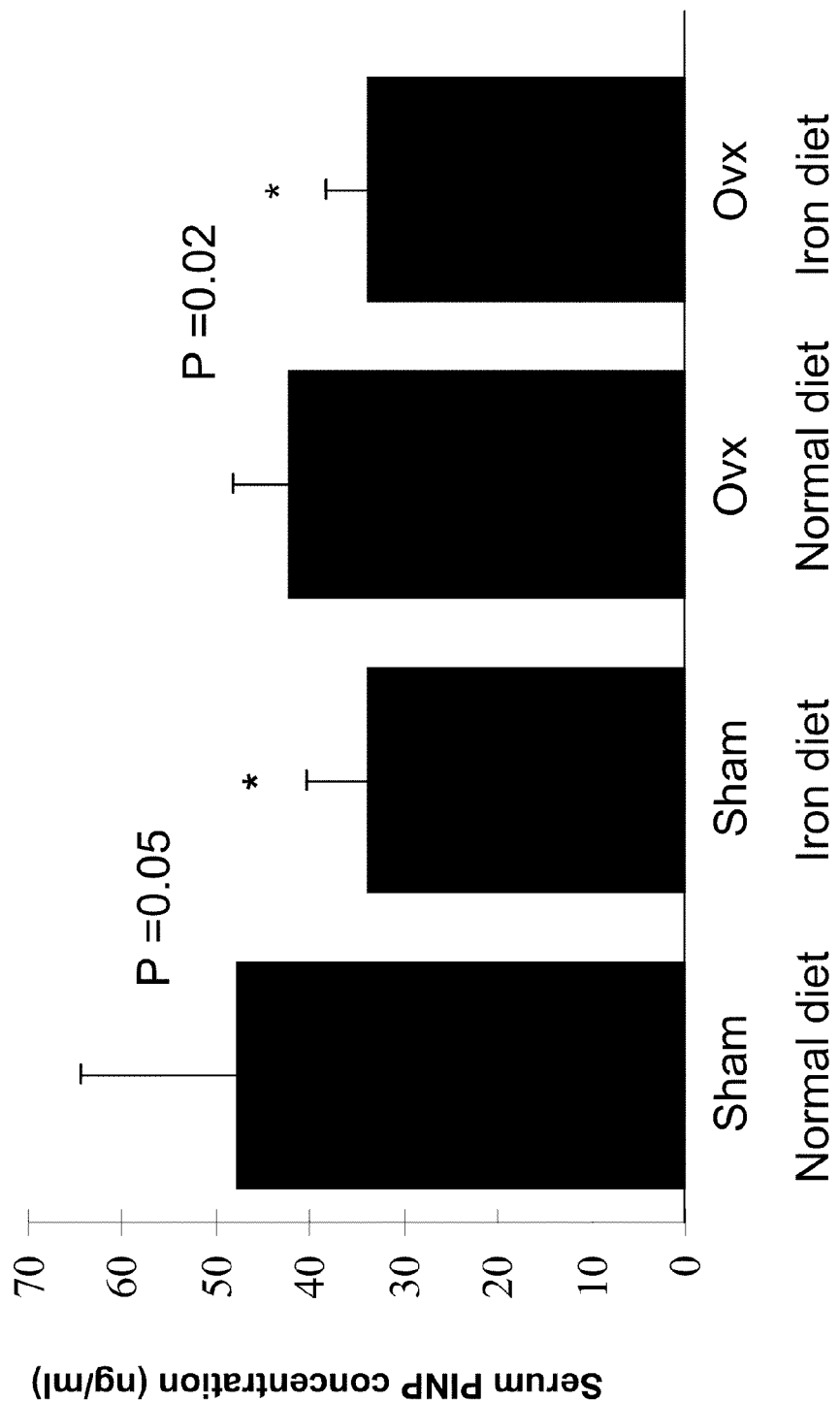
FIG. 29 shows significant differences in serum levels of amino-terminal propeptide of type I collagen (PINP), a bone formation marker, between iron-enriched diet and normal diet regardless of the estrogen status (n=10 per group).

FIG. 28 indicates that the body weight of the mice were neither affected by the ovariectomy (OVX) nor by the iron-enriched diet. It is interesting to note that serum levels of amino-terminal propeptide of type I collagen (PINP), a bone formation marker, were significantly lower in mice fed iron-enriched diet as compared to the mice fed normal diet (FIG. 29). Estrogen deficiency caused by OVX had no effects on PINP. These results provide further confirmation of the in vitro cell culture data that indicated that increased iron affects bone formation. Thus, the mode of action of increased iron as a result of menopause is different from that of estrogen deficiency, which mainly increases bone resorption.

Taken together, it can be concluded that increased iron as a result of cessation of menstruation is a new risk factor that has not yet been accounted for postmenopausal osteoporosis. Increased iron slows down bone formation by inhibiting osteoblast maturation as well as decrease E2 lifespan by promoting estrogen metabolism. The effects of increased iron on osteoblasts appear to be independent of estrogen deficiency and contribute to peri- and postmenopausal osteoporosis in a mode of action that is different from estrogen. The present invention provides an excellent opportunity to use hepcidin as a drug modulating body iron levels.

Although preferred embodiments have been depicted and described in detail herein, it will be apparent to those skilled in the relevant art that various modifications, additions, substitutions, and the like can be made without departing from the spirit of the invention and these are therefore, considered to be within the scope of the present invention as defined the claims which follow.

What is claimed:

1. A method of treating bone deterioration or osteoporosis in a peri- or post-menopausal female subject, said method comprising:
    selecting a peri- or post-menopausal female subject having bone deterioration or osteoporosis, and
    administering a hepcidin polypeptide to the selected subject under conditions effective to treat bone density or osteoporosis wherein the hepcidin polypeptide has the amino acid sequence of SEQ ID NO: 2.

2. The method according to claim 1, wherein the hepcidin polypeptide is human hepcidin.

3. The method according to claim 1, wherein the bone deterioration is in the form of a change in bone micro-architecture, decrease in calcium bioavailability, decrease in bone calcification rates, decrease in bone formation rates, decrease in osteoblast proliferation rates, decrease in differentiation rate of osteoblasts, and/or osteopeonia.

4. The method according to claim 1, wherein the subject is a mammal.

5. The method according to claim 1, wherein the subject is a human.

6. The method according to claim 1, wherein said administering is carried out orally, parenterally, subcutaneously, intravenously, intramuscularly, intraperitoneally, by intranasal instillation, or by application to mucous membranes.

7. The method according to claim 1, wherein the hepcidin is administered as a tablet, capsule, powder, solution, colloid, suspension, or emulsion.

* * * * *